United States Patent
Liu et al.

(10) Patent No.: US 9,949,695 B2
(45) Date of Patent: Apr. 24, 2018

(54) PHOTOELECTRIC TYPE PULSE SIGNAL MEASURING METHOD AND APPARATUS

(71) Applicant: Goertek Inc., Weifang (CN)

(72) Inventors: Song Liu, Weifang (CN); Shasha Lou, Weifang (CN); Bo Li, Weifang (CN)

(73) Assignee: GOERTEK INC., Weifang (CN)

( * ) Notice: Subject to any disclaimer, the term of this patent is extended or adjusted under 35 U.S.C. 154(b) by 0 days.

(21) Appl. No.: 15/126,873

(22) PCT Filed: Aug. 3, 2015

(86) PCT No.: PCT/CN2015/085949
§ 371 (c)(1),
(2) Date: Sep. 16, 2016

(87) PCT Pub. No.: WO2016/107171
PCT Pub. Date: Jul. 7, 2016

(65) Prior Publication Data
US 2017/0112448 A1   Apr. 27, 2017

(30) Foreign Application Priority Data
Dec. 31, 2014 (CN) .......................... 2014 1 0851383
Dec. 31, 2014 (CN) .......................... 2014 1 0852910

(51) Int. Cl.
A61B 5/00 (2006.01)
A61B 5/024 (2006.01)

(52) U.S. Cl.
CPC .............. *A61B 5/725* (2013.01); *A61B 5/024* (2013.01); *A61B 5/6803* (2013.01);
(Continued)

(58) Field of Classification Search
CPC ........ A61B 5/024; A61B 5/725; A61B 5/6803
See application file for complete search history.

(56) References Cited

U.S. PATENT DOCUMENTS 4,258,719 A    3/1981  Lewyn
5,807,267 A *  9/1998  Bryars ............... A61B 5/02433
                                                       600/477
(Continued)

FOREIGN PATENT DOCUMENTS

CN    1933769      3/2007
CN    102065749    5/2011
(Continued)

OTHER PUBLICATIONS

Kovačević et al., Adaptive Digital Filters, "Chapter 2 Adaptive Filtering", pp. 31-73, Academic Mind Belgrade and Springer-Verlag Berlin Heidelberg 2013.*
(Continued)

*Primary Examiner* — Tse Chen
*Assistant Examiner* — Joanne Hoffman
(74) *Attorney, Agent, or Firm* — Harness, Dickey & Pierce, P.L.C.

(57) ABSTRACT

A photoelectric type pulse signal measuring method includes, obtaining a main-path light signal transmitted by a photoelectric transmitter and reflected back from a surface of skin having an artery underneath, obtaining at least one auxiliary-path light signal receiving an ambient light signal, and based on the at least one auxiliary-path light signal, adaptively filtering an ambient light interference from the main-path light signal and obtaining an adaptive filtration result; or obtaining at least one auxiliary-path light signal transmitted by the same photoelectric transmitter and reflected back from a surface of skin without any artery underneath, and based on the auxiliary-path light signal, adaptively filtering a motion interference from the main-path light signal; then extracting a pulse signal from the adaptive filtration result. The present invention can simply and effectively eliminate the ambient light interference or motion (Continued)

interference upon photoelectric pulse signal measurement. Photoelectric type pulse signal measuring devices are also disclosed.

12 Claims, 7 Drawing Sheets

(52) U.S. Cl.
CPC .......... *A61B 5/7207* (2013.01); *A61B 5/7282* (2013.01); *A61B 5/6831* (2013.01)

(56) References Cited

U.S. PATENT DOCUMENTS

| | | | |
|---|---|---|---|
| 5,846,190 | A | 12/1998 | Woehrle |
| 5,885,213 | A | 3/1999 | Richardson et al. |
| 9,044,149 | B2 | 6/2015 | Richards et al. |
| 2006/0264721 | A1 | 11/2006 | Petersen et al. |
| 2008/0208066 | A1 | 8/2008 | Cinbis et al. |
| 2010/0217102 | A1* | 8/2010 | LeBoeuf ................ A61B 5/00 600/310 |
| 2011/0105867 | A1 | 5/2011 | Schultz et al. |

FOREIGN PATENT DOCUMENTS

| | | |
|---|---|---|
| CN | 102247124 | 11/2011 |
| CN | 102512175 A | 6/2012 |
| CN | 102512178 | 6/2012 |
| CN | 104161505 | 11/2014 |
| CN | 104207761 | 12/2014 |
| CN | 104586370 | 5/2015 |
| CN | 104706336 | 6/2015 |
| EP | 0319159 | 11/1988 |

OTHER PUBLICATIONS

Jaafari, "Adaptive Filtering for Heart Rate Signals" (May 2014). Master's Theses. Paper 4420, pp. 1-85.*

Tamura, Maeda, Sekine, Yohsida, "Wearable Photoplethysmographic Sensors—Past and Present", Electronics, Mar. 2014, pp. 282-302.*

E, Dong, et al., "Design on ear photoplethysmography sensor with movement interference cancellation," Aug. 31, 2012 (4 pages).

Zang, Hong, et al., "The Study on the Adaptive Filtering Method for Eliminating the Motion Artifact in Pulse Oximetry Measurement," Mar. 2001 (4 pages).

* cited by examiner

```
┌─────────────────────────────────────────────────────────────┐
│ Obtain a main-path light signal transmitted by a photoelectric │
│ transmitter and reflected back from a surface of skin having an │──S110
│ artery underneath, and obtain at least one auxiliary-path light │
│ signal for receiving an ambient light signal                    │
└─────────────────────────────────────────────────────────────┘
                              │
                              ▼
┌─────────────────────────────────────────────────────────────┐
│ Based on the at least one auxiliary-path light signal,         │
│ adaptively filter ambient light interference from the main-path │──S120
│ light signal and obtain an adaptive filtration result          │
└─────────────────────────────────────────────────────────────┘
                              │
                              ▼
┌─────────────────────────────────────────────────────────────┐
│ Extract a pulse signal from the adaptive filtration result     │──S130
└─────────────────────────────────────────────────────────────┘
```

Fig. 1

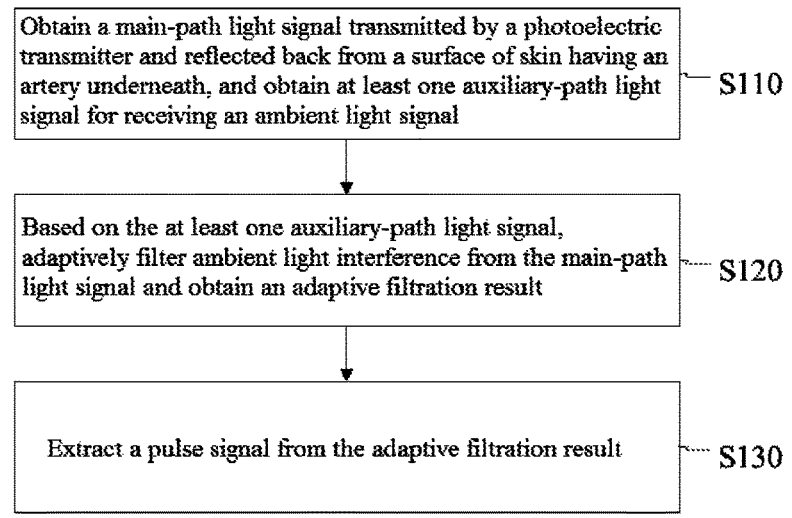

Fig. 2

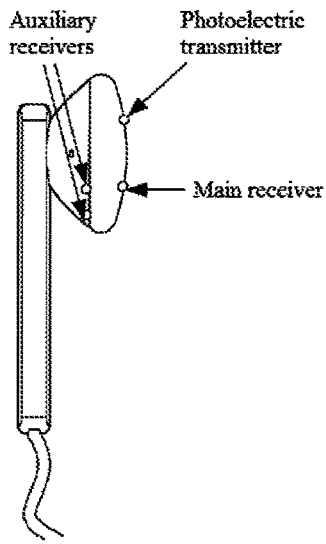

Fig. 3

PHOTOELECTRIC TYPE PULSE SIGNAL MEASURING METHOD AND APPARATUS

FIELD OF THE DISCLOSURE

The present disclosure relates to the technical field of signal detection, and particularly to a photoelectric type pulse signal measuring method and apparatus which can suppress noise interference and enhance intensity of the pulse detection signal.

BACKGROUND OF THE DISCLOSURE

The photoelectric type pulse signal detection is extensively applied to the field of medical care and consumer electronics, and particularly applied to wearable devices due to its characteristics such as convenient use, small size and low power consumption.

A main principle of photoelectric type pulse signal detection is that when light is irradiated on skin, it is partly absorbed and partly reflected; when heart beats, a flow rate of arterial blood in arterial blood vessels presents a periodic motion identical with a heartbeat cycle, which causes cyclic changes of the intensity of the reflected light. A photoelectric transmitter transmits light beams to the skin, the light beams are reflected by the skin and received by a photoelectric receiver, and a cycle and frequency of heartbeat may be obtained according to a change tendency of the intensity of the reflected light.

In practical application, the photoelectric type pulse detection is usually confronted with interference from ambient light. Natural light and artificial light outside a photoelectric sensor is irradiated on the photoelectric receiver to form ambient light interference. In practical application, the photoelectric type pulse detection are further vulnerable to the interference of a user's actions. For example, when it is applied to a smart watch or smart wristband, it is susceptible to the interference of a hand's motion. When it is applied to a smart earphone, it is susceptible to the interference of the head motions and respiration. Relative motion between a photoelectric pulse measuring instrument and skin causes an optical transmission pathway between the photoelectric transmitter and photoelectric sensor to change, causes changes of light intensity, and forms motion interference. The resultant ambient light interference and/or motion interference affect signal energy statistics of the reflected light and thereby affect a heartbeat cycle detection precision.

In conventional technologies, a customary method of eliminating and weakening ambient light interference is to improve the structure and minimize a gap between the optical sensor and the external environment to block the ambient light; another customary method is to strengthen a transmission intensity of a light source. However, these methods are less applicable in a portable device and a wearable device. In such devices, for the sake of convenience and comfort in use, contact between the sensor and skin is not tight, a gap is apt to occur, and a size of the gap varies with relative motions so that the ambient light is hard to effectively block; in a wearable device, the apparatus needs to operate in a longer time period, so increasing the light source intensity will cause excessive power consumption, and shorten the use time period, which is not applicable.

In conventional technologies, a customary method of eliminating and weakening motion interference is to strengthen the clamp or contact of the photoelectric sensor and skin to eliminate the motion interference. However, for a wearable device, the sensor cannot tightly contact with the skin and the body motion is frequent, so this method is not practical; another customary method is using an accelerometer to detect actions so as to eliminate action interference in the photoelectric sensor signal. However, since the accelerometer and photoelectric sensor are different types of sensors, different signal collecting systems need to be configured, and rigid sample cycle consistency is required between the signal collecting systems. The correspondence relationship between the accelerometer signal and the optical signal is complicated so that complexity of the hardware and software is high.

SUMMARY OF THE DISCLOSURE

In view of the above, a main object of the present disclosure is to provide a photoelectric type pulse signal measuring method and apparatus which can simply and effectively eliminate ambient light interference or motion interference upon pulse signal measurement.

To achieve the above object, technical solutions of embodiments of the present disclosure are implemented as follows:

In one aspect, embodiments of the present disclosure provide a photoelectric type pulse signal measuring method, the method comprising:

obtaining a main-path light signal transmitted by a photoelectric transmitter and reflected back from a surface of skin having an artery underneath, and obtaining at least one auxiliary-path light signal for receiving an ambient light signal;

based on the at least one auxiliary-path light signal, adaptively filtering ambient light interference from the main-path light signal and obtaining an adaptive filtration result;

extracting a pulse signal from the adaptive filtration result.

In an embodiment, a wearable measuring apparatus is provided with three or more photoelectric receivers, wherein one of the photoelectric receivers is a main receiver and the remaining photoelectric receivers are auxiliary receivers, and one of the auxiliary receivers, between which and the photoelectric transmitter no any artery passes, is used to receive an auxiliary-path light signal reflected back from a surface of skin without any artery underneath; the method further comprises:

obtaining the at least one auxiliary-path light signal transmitted by the same photoelectric transmitter and reflected back from a surface of skin without any artery underneath;

based on the at least one auxiliary-path light signal, adaptively filtering ambient light interference and motion interference from the main-path light signal to obtain an adaptive filtration result.

In another aspect, embodiments of the present disclosure provide a photoelectric type pulse signal measuring method, the method comprising:

obtaining a main-path light signal transmitted by a photoelectric transmitter and reflected back from a surface of skin having an artery underneath, and obtaining at least one auxiliary-path light signal transmitted by the photoelectric transmitter and reflected back from a surface of skin without any artery underneath;

based on the at least one auxiliary-path light signal, adaptively filtering motion interference from the main-path light signal to obtain an adaptive filtration result; and extracting a pulse signal from the adaptive filtration result.

In another aspect, embodiments of the present disclosure provide a measuring apparatus, comprising a photoelectric type pulse signal measuring device.

The measuring apparatus is provided with a photoelectric transmitter and two or more photoelectric receivers, wherein one of the photoelectric receivers is a main receiver and the remaining photoelectric receiver(s) is(are) auxiliary receiver(s).

The photoelectric type pulse signal measuring device comprises:

a light signal obtaining unit configured to obtain a main-path light signal transmitted by a photoelectric transmitter and reflected back from a surface of skin having an artery underneath, and obtain at least one auxiliary-path light signal for receiving an ambient light signal;

an adaptive filter unit configured to, based on the at least one auxiliary-path light signal, adaptively filter ambient light interference from the main-path light signal and obtain an adaptive filtration result;

a pulse signal extracting unit configured to extract a pulse signal from the adaptive filtration result.

When a user wears the measuring apparatus to measure a pulse signal, the main receiver and the photoelectric transmitter are placed respectively at a specified position of the skin, at least one artery passes between the main receiver and the photoelectric transmitter, each auxiliary receiver faces toward external environment, a distance between each auxiliary receiver and the photoelectric transmitter is larger than a distance threshold so that reflected light generated by the photoelectric transmitter does not enter the auxiliary receiver;

Or the photoelectric type pulse signal measuring device comprises:

a light signal obtaining unit configured to obtain a main-path light signal transmitted by a photoelectric transmitter and reflected back from a surface of skin having an artery underneath, and obtain at least one auxiliary-path light signal transmitted by the photoelectric transmitter and reflected back from a surface of skin without any artery underneath;

an adaptive filter unit configured to, based on the at least one auxiliary-path light signal, adaptively filter motion interference from the main-path light signal to obtain an adaptive filtration result; and a pulse signal extracting unit configured to extract a pulse signal from the adaptive filtration result.

When a user wears the measuring apparatus to measure a pulse signal, the main receiver and the photoelectric transmitter are placed respectively at a specified position of the skin, at least one artery passes between the main receiver and the photoelectric transmitter, and no artery passes between each auxiliary receiver and the photoelectrical transmitter.

As compared with the prior art, advantageous effects of the present invention are as follows:

The technical solutions of embodiments of the present disclosure comprise: based on a light propagation model and physical characteristics of a light intensity signal, by using photoelectric sensor array technology, obtaining a main-path light signal transmitted by a photoelectric transmitter and reflected back from a surface of skin having an artery underneath, obtaining at least one auxiliary-path light signal receiving an ambient light signal, and then based on the auxiliary-path light signal, adaptively filtering the ambient light interference signal from the main-path light signal so as to eliminate or reduce ambient light interference upon photoelectric detection of the pulse signal and improve the precision of pulse signal detection. Alternatively, obtaining a main-path light signal transmitted by a photoelectric transmitter and reflected back from a surface of skin having an artery underneath, obtaining at least one auxiliary-path light signal transmitted by the same photoelectric transmitter and reflected back from a surface of skin without any artery underneath, and then based on the auxiliary-path light signal, adaptively filtering the motion interference signal from the main-path light signal so as to eliminate or reduce the motion interference upon photoelectric detection of the pulse signal and improve the precision of pulse signal measurement. By using the photoelectric array to adaptively remove the ambient light interference or motion interference from the photoelectric signal without need to rigidly limit the contact degree of the apparatus and skin, the present technical solution can simply and effectively eliminate the ambient light interference or motion interference upon photoelectric pulse signal measurement. In addition, the present solution does not require high-intensity light source, and can reduce the power consumption of the measuring apparatus, and prolong the service life. Meanwhile, the input to be processed by the present solution is the photoelectric signal of the same type, and may be implemented by using the same signal sampling system and sampling cycle, thereby simplifying the complexity of the measuring system and substantially reducing data operation quantity.

BRIEF DESCRIPTION OF DRAWINGS

The drawings are used to provide further understanding of the present disclosure, constitute part of the description, are used together with embodiments of the present disclosure to illustrate the present disclosure, and are not construed to limit the present disclosure. In the drawings, FIG. 1 is a flow chart of a photoelectric type pulse signal measuring method according to an embodiment of the present disclosure;

FIG. 2 is a schematic view of a smart wristband according to an embodiment of the present disclosure;

FIG. 3 is a schematic view of a smart earphone according to an embodiment of the present disclosure;

DETAILED DESCRIPTION OF PREFERRED EMBODIMENTS

Figure 4:
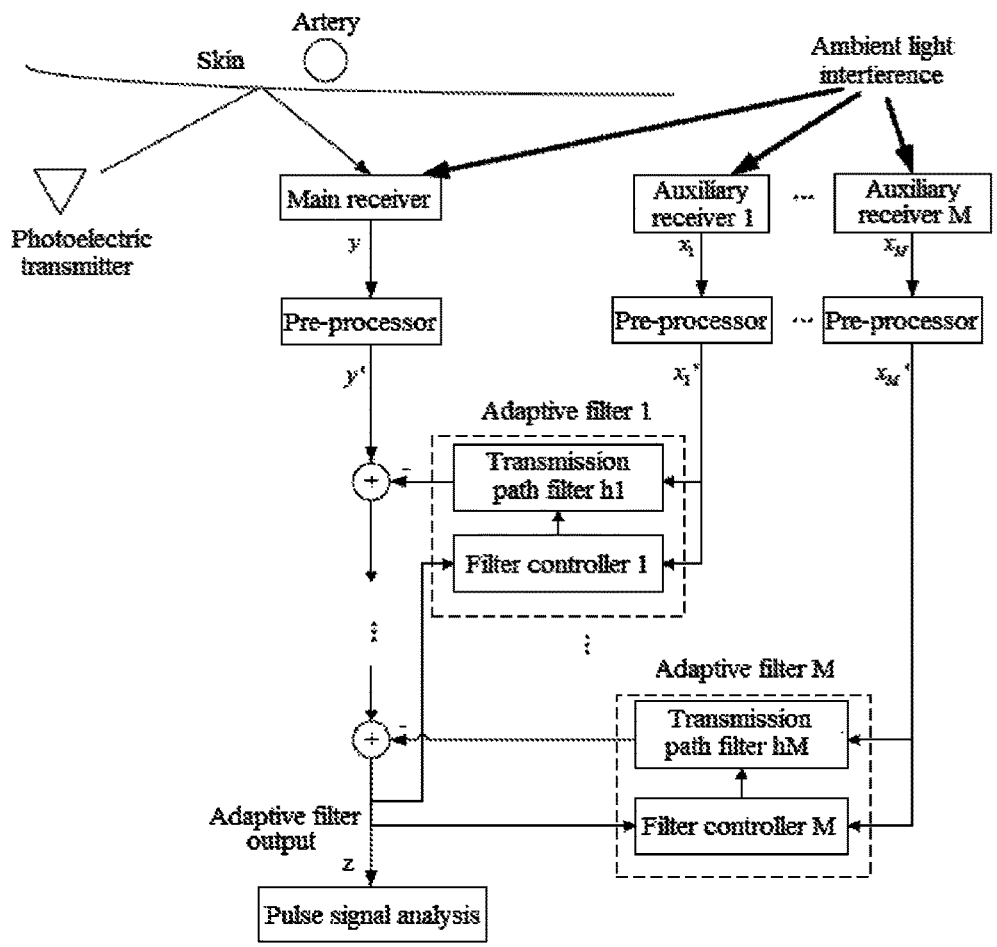
FIG. 4 is a schematic view of a photoelectric sensor array signal processing structure according to an embodiment of the present disclosure.

Embodiments of the present disclosure will be described hereunder in more detail with reference to figures to make objects, technical solutions and advantages of the present disclosure more apparent.

A main technical idea of the present disclosure lies in, by using photoelectric sensor array technology, based on physical characteristics of a light propagation model and light intensity signal, obtaining a main-path light signal transmitted by a photoelectric transmitter and reflected back from a surface of skin having an artery underneath, and obtaining at least one auxiliary-path light signal receiving an ambient light signal; based on the auxiliary-path light signal, adaptively filtering the ambient light signal in the main-path light signal so as to eliminate or reduce ambient light interference upon photoelectric detection of the pulse signal. Alternatively, based on an auxiliary-path light signal transmitted by the same photoelectric transmitter and reflected back from a surface of skin without any artery underneath, adaptively filtering motion interference from a main-path light signal reflected back from a surface of skin having an artery underneath, so as to eliminate or reduce the motion interference upon photoelectric detection of the pulse signal.

FIG. 1 is a flow chart of a photoelectric type pulse signal measuring method according to an embodiment of the present disclosure. Referring to FIG. 1, the photoelectric type pulse signal measuring method according to the embodiment of the present disclosure comprises:

Step S110: obtaining a main-path light signal transmitted by a photoelectric transmitter and reflected back from a surface of skin having an artery underneath, and obtaining at least one auxiliary-path light signal receiving an ambient light signal.

In a specific embodiment, the main-path light signal and auxiliary-path light signals may be obtained in the following manner:

A wearable measuring apparatus is provided with a photoelectric transmitter and two or more photoelectric receivers, wherein one photoelectric receiver is a main receiver and the remaining photoelectric receivers are auxiliary receivers; when the user wears the measuring apparatus to measure the pulse signal, the main receiver and the photoelectric transmitter are placed at a specified position of the skin. The specified position is configured in a way that at least one artery passes between the main receiver and the photoelectric transmitter, the auxiliary receivers face toward external environment, a distance between each auxiliary receiver and photoelectric transmitter is larger than a distance threshold so that the reflected light generated by the photoelectric transmitter does not enter the auxiliary receivers; the main receiver is used to receive a light signal transmitted by the photoelectric transmitter and reflected back from a surface of skin having an artery underneath, and the auxiliary receivers are used to receive the ambient light signal.

The wearable measuring apparatus may specifically be, but not limited to a measuring apparatus such as a smart wristband and a smart earphone which utilizes the present solution and in which a photoelectric pulse measuring instrument is built. The present solution may be applied to other wearable electronic products which require performance of pulse detection.

FIG. 2 is a schematic view of a smart wristband according to an embodiment of the present disclosure. As shown in FIG. 2, the smart wristband is provided with an photoelectric transmitter and three photoelectric receivers including one main receiver and two auxiliary receivers, wherein the user duly wears the wristband to measure the pulse, the main receiver and the photoelectric transmitter are arranged on inside where the smart wristband contacts with wrist skin, and at least one artery is located between the main receiver and the photoelectric transmitter. The two auxiliary receivers face towards the external environment at a location farther away from the photoelectric transmitter and are arranged on the outside where the smart wristband does not contact with the wrist skin. Specifically, the two auxiliary receives may be disposed on a lateral edge of the smart wristband, and no artery passes between the two auxiliary receivers and the photoelectric transmitter.

FIG. 3 is a schematic view of a smart earphone according to an embodiment of the present disclosure. As shown in FIG. 3, the smart earphone is provided with a photoelectrical transmitter and three photoelectric receivers including one main receiver and two auxiliary receivers, wherein when the user duly wears the earphone to measure the pulse, the photoelectric transmitter and the main receiver are arranged at a position on an earplug contacting with ear skin, and at least one artery passes between the main receiver and the photoelectric transmitter. The two auxiliary receivers are arranged at a position of the earplug not contacting with the ear skin, specifically disposed at an outer edge of the earplug of the smart earphone, and located farther away from the photoelectric transmitter, and face towards the external environment. No artery passes between the two auxiliary receivers and the photoelectric transmitter.

Step S120: based on the at least one auxiliary-path light signal, adaptively filtering the ambient light interference in the main-path light signal and obtaining an adaptive filtration result.

Specifically, the adaptive filtering operation in step S120 may comprise a plurality of adaptive filtering cycles, operation of each adaptive filtering cycle comprising:

obtaining a transmission path filter of each auxiliary-path light signal according to light intensity relationship between ambient light in each auxiliary-path light signal and ambient light in the main-path light signal; in one adaptive filtering cycle, calculating output signals of each auxiliary-path light signal passing through respective transmission path filter; subtracting output signals of the auxiliary-path light signals from the main-path light signal to obtain a filtration result output in this adaptive filtering cycle.

After a filtration result output in this adaptive filtering cycle is obtained, the step S120 may further comprise:

calculating an update amount of transmission path filter coefficients of each auxiliary-path light signal according to a relevant function of the filtration result in this adaptive filtering cycle and each auxiliary-path light signal; adding the update amount correspondingly to the transmission path filter coefficients of each auxiliary-path light signal, and updating the transmission path filter of each auxiliary-path light signal to obtain a transmission path filter of each auxiliary-path light signal in next adaptive filtering cycle.

After updating the transmission path filters of the auxiliary-path light signals in each adaptive filtering cycle, the step S120 may further comprise:

judging whether the updated transmission path filter satisfies a filter constraint condition, taking the updated transmission path filter as a transmission path filter of the auxiliary-path light signal in next adaptive filtering cycle if the updated transmission path filter satisfies the filter constraint condition, and performing normalization processing for the updated transmission path filter if the updated transmission path filter does not satisfy the filter constraint condition, and taking the normalized transmission path filter as a transmission path filter of the auxiliary-path light signal in next adaptive filtering cycle.

When calculating that the update amount of the transmission path filter coefficients of an auxiliary-path light signal is smaller than an update threshold, confirming that the auxiliary receiver achieves accurate tracing of the ambient light.

Step S130: extracting a pulse signal from the adaptive filtration result.

After the processing in the step S120, among the adaptive filtration result obtained by adaptively filtering ambient light interference from the main-path light signal, most signals are signals relevant to the pulse signal, and the pulse signal may be extracted therefrom to perform ECG analysis.

According to the photoelectric type pulse signal measuring method according to the embodiment of the present disclosure, the photoelectric sensor array technology is utilized, the ambient light interference is adaptively filtered from the main-path light signal, the contact degree between the apparatus and skin is not limited rigidly, and ambient light interference upon the photoelectric type pulse signal measurement can be eliminated simply and effectively.

In a preferred embodiment, the auxiliary-path light signals and the main-path light signal are pre-processed before the ambient light interference is adaptively filtered from the main-path light signal based on the auxiliary-path light signals. The pre-processing may be completed by a pre-processor in practice. The pre-processed content comprises:

filtering a direct current component and a high-frequency component from the main-path light signal and auxiliary-path light signals; performing frequency energy equalization related to the pulse signal respectively for the main-path light signal and auxiliary-path light signals from which the direct current component and high-frequency component are filtered.

The main-path light signal and auxiliary-path light signals after going through the above-pre-processing enter the adaptive filters, and the adaptive filtration result after the ambient light interference is adaptively filtered can be more accurately obtained.

The principle of the photoelectric type pulse signal measuring method according to the embodiment of the present disclosure will be illustrated with reference to FIG. 4. FIG. 4 is a schematic view of a photoelectric sensor array signal processing structure according to an embodiment of the present disclosure.

Referring to FIG. 4, the photoelectric sensor array comprises a plurality of photoelectric receivers and a photoelectric transmitter, wherein the photoelectric receivers comprise one main receiver and a plurality of auxiliary receivers. The light beam transmitted by the photoelectric transmitter is irradiated on skin, the main receiver is used to receive the light signal reflected back from a surface of skin having an artery underneath, components of the signal comprise pulse signal and ambient light interference, M auxiliary receivers are used to receive the ambient light signal which substantially only includes ambient light interference component. Upon application to the photoelectric type pulse signal measuring apparatus, when the user duly wears the measuring apparatus, the main receiver and the photoelectric transmitter are arranged at a specified position on the apparatus closer to the skin, and at least one artery passes between the main receiver and the photoelectric transmitter. The auxiliary receivers are arranged facing toward external environment, farther away from the photoelectric transmitter, and no artery passes between the auxiliary receives and the photoelectric transmitter.

The signal of the photoelectric receiver array is processed by software algorithm, the signal of the main receiver and the signals of the auxiliary receivers are subjected to pre-processing, the pre-processed signals of the auxiliary receivers go through the adaptive filters to eliminate the ambient light interference from the pre-processed signal of the main photoelectric receiver. The output signal after the ambient light interference is eliminated from the main receiver signal may be used for pulse signal analysis and extraction.

To enable adaptive filtration of the ambient light interference from the main-path light signal, the solution of the present disclosure is divided into several basic parts: pre-processor and adaptive filter, wherein the adaptive filter of each auxiliary receiver comprises a transmission path filter and a filter controller. What is received by the photoelectric receivers is light intensity signal, signals y, $x_1, x_2, \ldots, x_M$ of the main and auxiliary receivers are respectively input into corresponding pre-processors for processing. The main and auxiliary receiver signals output by the pre-processors are $y', x_1', x_2', \ldots, x_M'$. The output $x_1', x_2', \ldots, x_M'$ of the pre-processors corresponding to the auxiliary receivers are respectively input into the adaptive filter of each auxiliary receiver. The ambient light interference in the main receiver signal $y'$ after the pre-processing is eliminated by using a result after the signals $x_1', x_2', \ldots, x_M'$ from the auxiliary receivers go through adaptive filtration. In the output signal z after the adaptive filtration, most of the ambient light interference is eliminated, and the signal output after the filtration is chiefly the pulse signal.

Based on the physical characteristics of the light propagation model and the light intensity signal, the signal y of the main receiver is divided into two parts: one part is light intensity signal $y_P$ carrying the pulse information (the light signal transmitted by the light transmitter, reflected by the skin surface and received by the main receiver); and the other part is ambient light interference $y_J$. The signals of the auxiliary receivers only include ambient light interference component, the reflected light reflected by the skin is farther from the auxiliary receivers, and due to limitation of the device structure, cannot reach the auxiliary receivers or only extremely little thereof reach the auxiliary receivers, and therefore may be neglected. That is, $$y = y_J + y_P$$

$$x_k = z_{Jk}$$

Wherein $y_P$ is the light intensity signal of the pulse information received by the main receiver, $y_J$ is the ambient light interference component received by the main receiver, $x_{Jk}$ is the ambient light interference component received by the auxiliary receiver k, y is the signal of the main receiver, and $x_k$ is the signal of the auxiliary receiver k.

A situation with only one auxiliary receiver is taken into account: an ambient light interference source J is propagated to the main receiver and auxiliary receiver k, and then an ambient light intensity signal $y_J$ propagated to the main receiver and a light intensity signal $x_{Jk}$ propagated to the auxiliary receiver k are in the following relation:

$$y_J = h_k * x_{Jk}$$

$h_k$ represents an energy change of the ambient light interference J transmitted from the auxiliary receiver k to the main receiver, and a transmission path filter is designed according to $h_k$. That is to say, the transmission path filters of the auxiliary-path light signals are obtained according to a light intensity change tendency of the ambient light in the auxiliary-path light signals and the main-path light signal. An order length L of $h_k$ depends on the transmission path and a sampling interval, for example, fifth order or tenth order may be selected.

Then there is the following equation:

$$y = h_k * x_{Jk} + y_P$$

In the case that there are M auxiliary receivers, $$y_J = \sum_{k=1}^{M} h_k * x_{Jk}$$

$$y = \sum_{k=1}^{M} h_k * x_{Jk} + y_P$$

If a plurality of transmission path filters $h_k$ can be estimated, the pulse signal $y_P$ can be solved according to a signal model and the main and auxiliary receiver signals.

In the wearable apparatus, as the wearing manner might change at any time, a change of $h_k$ is caused. Hence, a reasonable manner is allowing $h_k$ to be adaptively variable with the environment, so the adaptive filtering manner is employed.

In each operation cycle, a new signal enters the main and auxiliary receivers, after a procedure of pre-processing, filtering and filter updating, the pulse signal is the output of the adaptive filtration, and output to a subsequent level for pulse analysis.

Still referring to FIG. 4, specific implementation modes of the pre-processor and adaptive filter are as follows:

1. Pre-processor

The pre-processor functions to remove the direct current component and high-frequency component in the photoelectric receiver signal, and perform proper frequency component adjustment for the signal, specifically perform frequency energy equalization related to the pulse signal respectively for the main-path light signal and auxiliary-path light signals. The function of the pre-processing corresponds cascading of a bandpass filter and an equalizer.

A lower cutoff frequency of the bandpass filter is generally much lower than a healthy adult's heartbeat frequency, e.g., 0.1 Hz, and an upper cutoff frequency is generally much higher than a healthy adult's heartbeat frequency, e.g., 5 Hz.

The equalizer may be used to improve energy of a desired frequency component. The equalizer may be specifically implemented by a differential filter. For example, in some application, a rising edge and a falling edge of the pulse signal need to be detected, the high-frequency component needs to be raised relative to the low-frequency component, and the high-frequency component related to the pulse signal needs to be subjected to differential filtering processing.

This is because the high-frequency component can better characterize sudden changes of the detected signal, e.g., the rising edge and falling edge of the signal. Hence, upon detecting the heartbeat cycle and performing heartbeat signal analysis, a time point of the rising edge and falling edge of the pulse signal needs to be estimated accurately. Therefore, high-frequency component related to the pulse signal needs to be subjected to high-frequency lift.

Figure 5:
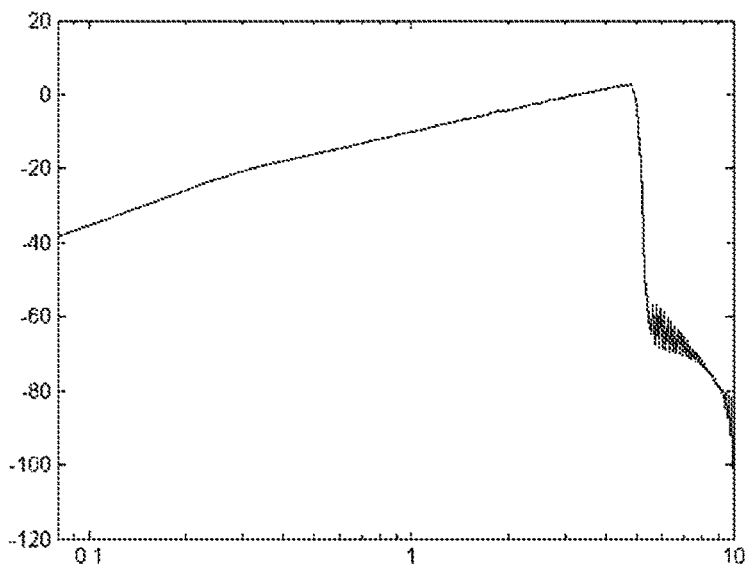
FIG. 5 is a typical pre-processor frequency response curve according to an embodiment of the present disclosure.

FIG. 5 is a typical pre-processor frequency response curve according to an embodiment of the present disclosure. A transverse axis in FIG. 1 is a frequency (in Hz) of the pre-processor, and a longitudinal axis is a frequency response (in dB) to a corresponding frequency of the pre-processor. The pre-processor is formed by cascading a bandpass filter in a frequency range of [0.1.5] Hz with a differential filter. As shown in FIG. 5, the high-frequency component is lifted in terms of frequency response (dB) relative to the low-frequency component.

2. Adaptive Filter

The adaptive filter is used to remove a signal component in the main receiver signal similar to the ambient light interference, and may be divided into two portions: a transmission path filter and a filter controller.

The transmission path filter is used to estimate a light intensity change tendency h when the ambient light interference reaches the main receiver from the auxiliary receivers, that is to say, the transmission path filter of each auxiliary-path light signal is obtained according to the light intensity relationship between the ambient light in the auxiliary-path light signal and the ambient light in the main-path light signal.

In an adaptive filtering cycle, output signals of the auxiliary-path light signals after undergoing corresponding transmission path filters are calculated; the output signals of the auxiliary-path light signals are subtracted from the main-path light signal to obtain a filtering result z output under this adaptive filtering cycle.

The filter controller is used to calculate a relevant function of the z signal and the signal of each auxiliary receiver, that is to say, an update amount of transmission path filter coefficients of each auxiliary-path light signal is calculated according to a relevant function of the filtration result in this adaptive filtering cycle and each auxiliary-path light signal (signal $x_k'$ of each auxiliary-path light signal undergoing the pre-processing). In this way, a proportion of the ambient light interference in the z signal can be determined to adjust the update amount of transmission path filter coefficients of each auxiliary receiver. Optionally, the above relevant function may be a relevant function of the filtration result in this adaptive filtering cycle and the signal of each auxiliary-path light signal undergoing the transmission path filter.

Regarding the transmission path filter $h_k$ of the $k^{th}$ auxiliary receiver, assume that its order length is L, its update amount $\Delta h_k$ is calculated in the following manner:

$$\Delta h_k(l) = \frac{x_k'(n - l + 1)z(n)}{E(x_k^2)},$$

$$L \geq l \geq 1$$

The update amount is added correspondingly to the transmission path filter coefficients of the auxiliary-path light signal, and the transmission path filters of the auxiliary-path light signals are updated to obtain transmission path filters of the auxiliary-path light signals in next adaptive filtering cycle. That is, the original filter is added with the update amount to obtain a new filter, which can be expressed by the following equation:

$$h_k(l)_{new} = h_k(l)_{old} + \Delta h_k(l)$$

Hereunder, illustration is presented still in combination with FIG. 4:

The pre-processed signals of the auxiliary receivers pass through the transmission path filters, and are subtracted one by one from the pre-processed main receiver signal to obtain an adaptive filter output signal z under an adaptive filtering cycle. Specifically, Assume that the transmission path filter of the $k^{th}$ auxiliary receiver is $h_k$, and n is a sampling serial number of the digital signal, the output z may be represented as follows:

$$z(n) = y'(n) - \sum_{k=1}^{M} x'_k(n) * h'_k(n)$$

The adaptive filter output z signal is the output of the system, z is the adaptive filter result, the pulse signal is extracted from z and may be transmitted to next level for pulse signal analysis.

Since the pulse signal analysis solution has a certain fault tolerance, in a processing manner of the present embodiment, the adaptive filter result obtained under each adaptive filter cycle is output in real time to facilitate subsequent pulse signal analysis and processing.

After the transmission path filters of the auxiliary-path light signals are updated, judgment is made as to whether the updated transmission path filters satisfy filter constraint condition. The updated transmission path filter is taken as a transmission path filter of the auxiliary-path light signal in next adaptive filtering cycle if the updated transmission path filter satisfies the filter constraint condition, and normalization processing for the updated transmission path filter is performed if the updated transmission path filter does not satisfy the filter constraint condition, and the normalized transmission path filter is taken as a transmission path filter of the auxiliary-path light signal in next adaptive filtering cycle. The reason is as follows:

Since the auxiliary receivers are closer to the ambient light interference, the intensity of the ambient light interference for the auxiliary receivers is higher than that for the main receiver. Hence, $$\sum_{l=1}^{L} h_k^2(l) < 1.$$

Therefore, the present embodiment employs the filter constraint condition that a sum of squares of transmission path filter coefficients is smaller than 1, to perform filter constraint for the solved transmission path filters. When the sum of squares of the coefficients of the filter is greater than 1, normalization processing needs to be performed for the filter. The normalization processing formula may be represented as follows:

$$h_k = h_k \bigg/ \max\left(1, \sqrt{\sum_{l=1}^{L} h_k^2(l)}\right)$$

The transmission path filers of all auxiliary receivers are updated in turn by this method.

The flow proceeds to next adaptive operation cycle upon completion of update of the transmission path filers of all auxiliary receivers.

When each calculated update amount of the transmission path filter coefficients of all auxiliary-path light signals is smaller than an update threshold, completion of adaptive filtering is confirmed to obtain the adaptive filtering result. At this time, the adaptive filtering reaches a dynamic balance state, the pulse signal extracted from the adaptive filter result is relatively stable and may be transmitted to next level for pulse signal analysis.

It is appreciated that in practical application, the photoelectric type pulse detection is also subjected to motion interference. The motion interference mainly refers to interference incurred by a light propagation path change between the light transmitting portion and receiving portion of the sensor caused by body motions. Regarding the above problem, based on the same inventive concept identical with elimination of ambient light interference upon photoelectric pulse signal measurement in the present disclosure as stated above, the present disclosure may use the photoelectric sensor array technology to further adaptively eliminate the motion interference upon photoelectric type pulse signal measurement based on the light propagation model and the physical characteristics of light intensity signal.

Figure 6:
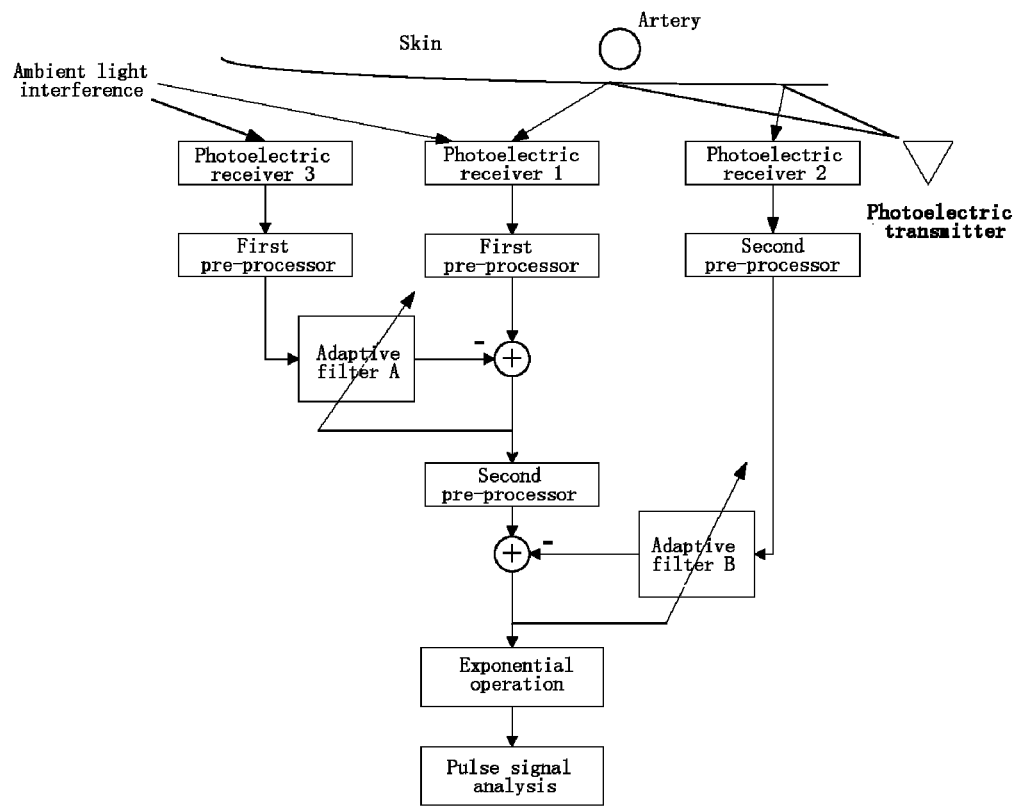
FIG. 6 is a schematic view of another photoelectric sensor array signal processing structure according to an embodiment of the present disclosure.

FIG. 6 is a schematic view of another photoelectric sensor array signal processing structure according to an embodiment of the present disclosure. Referring to FIG. 6, the photoelectric sensor array comprises three photoelectric receivers and a photoelectric transmitter. The light beam transmitted by the photoelectric transmitter is irradiated on skin, a photoelectric receiver 1 (main receiver) is used to receive a light signal reflected back from a surface of skin having an artery underneath, a photoelectric receiver 2 (auxiliary receiver) is used to receive a light signal reflected back from a surface of skin without any artery underneath, and a photoelectric receiver 3 (auxiliary receiver) is used to receive the ambient light signal. The signal received by the photoelectric receiver 1 is a mixed signal of a pulse signal, ambient light interference and motion interference, the signal received by the photoelectric receiver 2 is mostly action interference, and the signal received by the photoelectric receiver 3 is mostly ambient light interference. Since a logarithmic device might cause data error upon removal of motion interference, on an occasion that the ambient interference and motion interference need to be removed simultaneously, it is preferable to remove the environment interference first and then remove the motion interference. The output obtained from the operation of removing the environment interference serves as an input of the operation of removing the motion interference.

In the processing flow as shown in FIG. 6, the signals received by the three photoelectric receivers are all subjected to pre-processing, wherein the photoelectric receiver 1 and photoelectric receiver 3 undergo a first pre-processor to remove a direct current component and a high-frequency component, and the photoelectric receiver 2 undergoes a second pre-processor to perform logarithmic operation processing and filter a direct current component and a high-frequency component. In a first-level adaptive filtering, the signal of the photoelectric receiver 3 goes through an adaptive filter A to eliminate the ambient light interference in the photoelectric receiver 1 (main receiver) to obtain a first-level adaptive filter output signal. The first-level adaptive filter output signal, after going through the logarithmic operation processing by the second pre-processor, is input to a second-level filtering processing. The pre-processed signal of the photoelectric receiver 2 goes through the second pre-processor to perform logarithmic operation processing and filter the direct current component and high-frequency component, and then goes through an adaptive filter B to eliminate the action interference from the first-level adaptive filter output signal, and then goes through exponential operation to obtain a second-level adaptive filter output signal which may be used for pulse signal analysis and extraction.

Figure 7:
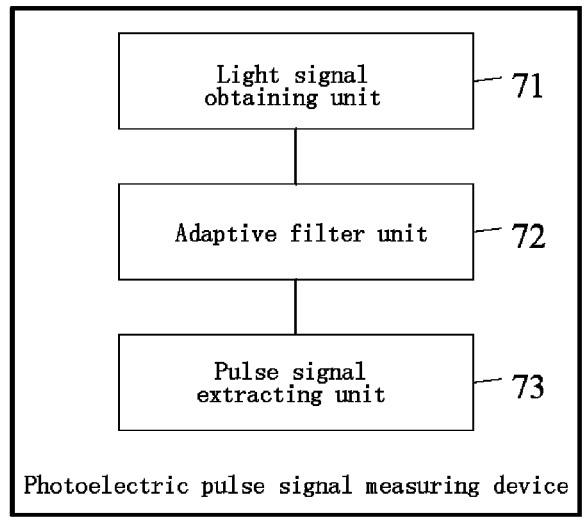
FIG. 7 is a block diagram of a photoelectric type pulse signal measuring device according to an embodiment of the present disclosure.

According to another aspect, the present disclosure further provides a photoelectric type pulse signal measuring device. FIG. 7 is a block diagram of a photoelectric type pulse signal measuring device according to an embodiment of the present disclosure. Referring to FIG. 7, the photoelectric type pulse signal measuring device according to an embodiment of the present disclosure comprises a light signal obtaining unit 71, an adaptive filter unit 72 and a pulse signal extracting unit 73.

The light signal obtaining unit 71 is configured to obtain a main-path light signal transmitted by a photoelectric transmitter and reflected back from a surface of skin having an artery underneath, and obtain at least one auxiliary-path light signal receiving an ambient light signal.

The adaptive filter unit 72 is configured to, based on the at least one auxiliary-path light signal, adaptively filter the ambient light interference in the main-path light signal and obtain an adaptive filtration result.

The pulse signal extracting unit 73 is configured to extract a pulse signal from the adaptive filtration result.

According to the photoelectric type pulse signal measuring device provided by the embodiment of the present disclosure, the photoelectric sensor array technology is utilized, the ambient light interference is adaptively filtered from the main-path light signal, the contact degree between the apparatus and skin is not limited rigidly, and ambient light interference upon the photoelectric type pulse signal measurement can be eliminated simply and effectively.

In a preferred embodiment, before the ambient light interference is adaptively filtered from the main-path light signal based on the auxiliary-path light signals, the auxiliary-path light signals and the main-path light signal are pre-processed to filter the direct current component and high-frequency component from the main-path light signal and auxiliary-path light signals, and further perform frequency energy equalization related to the pulse signal respectively for the main-path light signal and auxiliary-path light signals from which the direct current component and high-frequency component are filtered, and then transmit the main-path light signal and auxiliary-path light signals after having gone through the above-pre-processing to the adaptive filter unit to adaptively filter the ambient light interference from the main-path light signal to obtain the adaptive filtration result.

Figure 8:
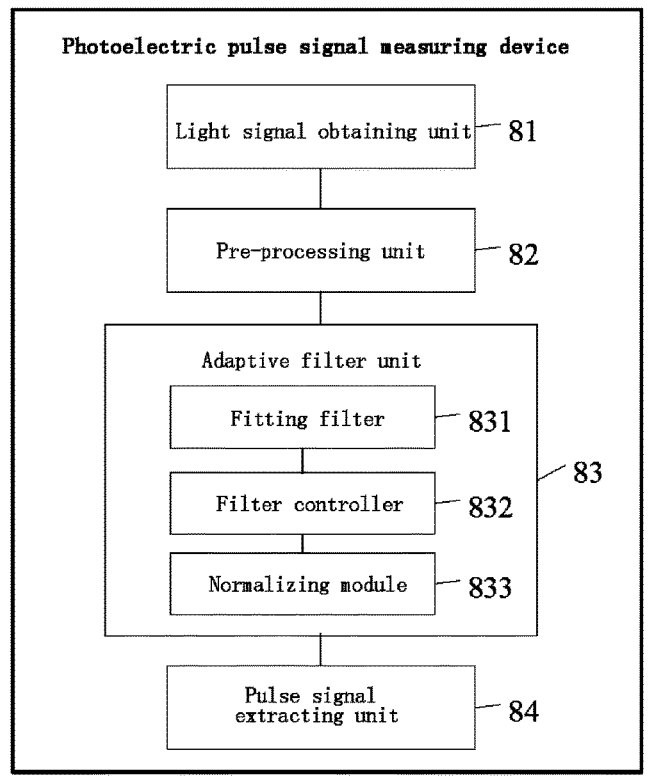
FIG. 8 is a block diagram of another photoelectric type pulse signal measuring device according to an embodiment of the present disclosure.

Specifically, referring to FIG. 8, FIG. 8 is a block diagram of another photoelectric type pulse signal measuring device according to an embodiment of the present disclosure. The photoelectric type pulse signal measuring device comprises: a light signal obtaining unit 81, a pre-processing unit 82, an adaptive filter unit 83 and a pulse signal extracting unit 84.

The light signal obtaining unit 81 is configured to obtain a main-path light signal transmitted by a photoelectric transmitter and reflected back from a surface of skin having an artery underneath, and obtain at least one auxiliary-path light signal receiving an ambient light signal.

The pre-processing unit 82 is configured to filter a direct current component and a high-frequency component from the main-path light signal and auxiliary-path light signals; preferably, the pre-processing unit 82 is further configured to perform frequency energy equalization related to the pulse signal respectively for the main-path light signal and auxiliary-path light signals from which the direct current component and high-frequency component are filtered.

The adaptive filter unit 83 is configured to, based on the at least one auxiliary-path light signal, adaptively filter the ambient light interference in the main-path light signal, and obtain an adaptive filtration result.

Specifically, the adaptive filter unit 83 comprises:

a transmission path filter 831 configured to obtain the transmission path filters of the auxiliary-path light signals according to a light intensity change tendency of the ambient light in the auxiliary-path light signals and the main-path light signal; in one adaptive filtering cycle, calculate output signals of the auxiliary-path light signals passing through respective transmission path filters; subtract output signals of the auxiliary-path light signals from the main-path light signal to obtain a filtration result output in this adaptive filtering cycle.

a filter controller 832 configured to calculate an update amount of transmission path filter coefficients of each auxiliary-path light signal according to a relevant function of the filtration result in this adaptive filtering cycle and each auxiliary-path light signal; add the update amount correspondingly to the transmission path filter coefficients of each auxiliary-path light signal, and update the transmission path filters of the auxiliary-path light signals to obtain transmission path filters of the auxiliary-path light signals in next adaptive filtering cycle.

a normalizing module 833 configured to judge whether the updated transmission path filter satisfies a filter constraint condition, take the updated transmission path filter as a transmission path filter of the auxiliary-path light signal in next adaptive filtering cycle if the updated transmission path filter satisfies the filter constraint condition, and perform normalization processing for the updated transmission path filter if the updated transmission path filter does not satisfy the filter constraint condition, and take the normalized transmission path filter as a transmission path filter of the auxiliary-path light signal in next adaptive filtering cycle.

The pulse signal extracting unit 84 configured to extract a pulse signal from the adaptive filtration result.

In the present embodiment, the pre-processing unit filters the direct current component and high-frequency component of the signal of photoelectric receivers and perform pre-processing like frequency energy equalization related to the pulse signal respectively for the main-path light signal and auxiliary-path light signals from which the direct current component and high-frequency component are filtered, to allow for more accurate adaptive filtration result after the ambient light interference is adaptively filtered from the main-path light signal.

According to a further aspect, embodiments of the present disclosure further provide a measuring apparatus, comprising the above-mentioned photoelectric type pulse signal measuring device.

The measuring apparatus is provided with a photoelectric transmitter and two or more photoelectric receivers, wherein one photoelectric receiver is a main receiver and the remaining photoelectric receivers are auxiliary receivers.

When the user wears the measuring apparatus to measure the pulse signal, the main receiver and the photoelectric transmitter are placed at a specified position of the skin. At least one artery passes between the main receiver and the photoelectric transmitter, the auxiliary receivers face toward external environment, a distance between each auxiliary receiver and photoelectric transmitter is larger than a distance threshold so that the reflected light generated by the photoelectric transmitter does not enter the auxiliary receivers.

In practical use, the measuring apparatus is preferably an annular apparatus adapted to a human wrist, wherein the photoelectric transmitter and the main photoelectric receiver are arranged on inside where the annular apparatus contacts with the wrist skin, the auxiliary receivers are arranged on outside where the annular apparatus does not contact with the wrist skin. Specifically, the auxiliary receivers may be disposed at a lateral edge of the annular apparatus facing towards the external environment. Certainly, the measuring apparatus may also be an earphone. The main photoelectric receiver and the photoelectric transmitter are arranged at a position on an earplug contacting with ear skin, the auxiliary receivers are arranged at positions of the earplug not contacting with the ear skin, specifically the auxiliary receivers are disposed on a housing of the earplug of the earphone to face towards the external environment. The present technical solution exemplarily provides the above two types of measuring apparatus. Noticeably, the present disclosure by no means limits the designed structure of the measuring apparatus so long as the photoelectric sensor array technology can be used to perform corresponding adaptive filter processing for the signals of the photoelectric transmitter and photoelectric receivers so as to eliminate the ambient light interference upon photoelectric type pulse signal measurement, and improve the precision of the pulse signal detection.

Figure 9:
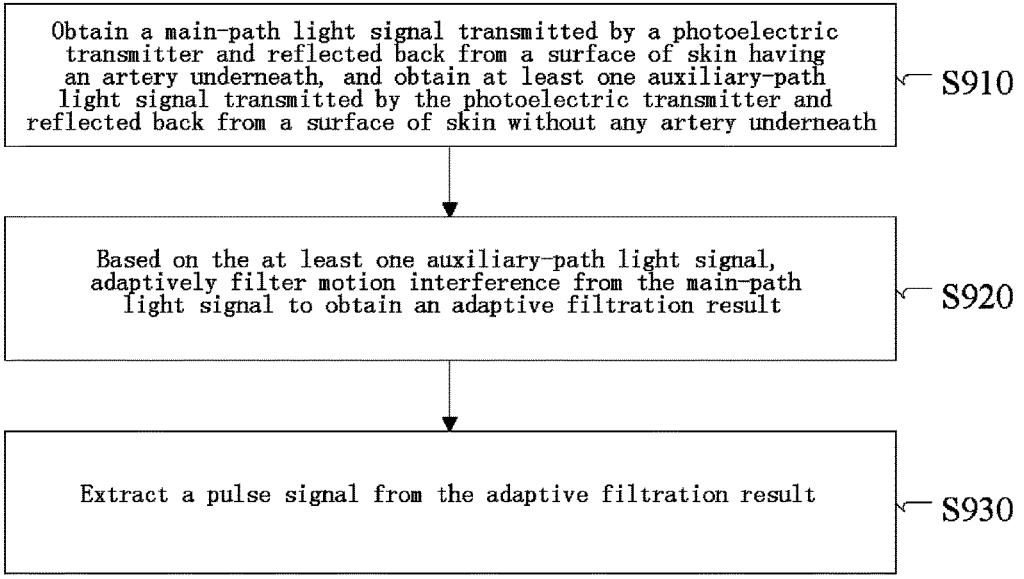
FIG. 9 is a flow chart of another photoelectric type pulse signal measuring method according to an embodiment of the present disclosure.

FIG. 9 is a flow chart of another photoelectric type pulse signal measuring method according to an embodiment of the present disclosure. Referring to FIG. 9, the photoelectric type pulse signal measuring method according to the embodiment of the present disclosure comprises:

Step S910: obtaining a main-path light signal transmitted by a photoelectric transmitter and reflected back from a surface of skin having an artery underneath, and obtaining at least one auxiliary-path light signal transmitted by the same photoelectric transmitter and reflected back from a surface of skin without any artery underneath.

In a specific embodiment, the main-path light signal and auxiliary-path light signals may be obtained in the following manner:

A wearable measuring apparatus is provided with a photoelectric transmitter and two or more photoelectric receivers, wherein one photoelectric receiver is a main receiver and the remaining photoelectric receivers are auxiliary receivers; when the user wears the measuring apparatus to measure the pulse signal, the main receiver and the photoelectric transmitter are placed at a specified position of the skin. The specified position is configured in a way that at least one artery is located between the main receiver and the photoelectric transmitter, and no artery passes between the auxiliary receivers and the photoelectric transmitter; the main receiver is used to receive a light signal transmitted by the photoelectric transmitter and reflected back from a surface of skin having an artery underneath, and the auxiliary receivers are used to receive light signal reflected back from a surface of skin without any artery underneath.

The wearable measuring apparatus may specifically be, but not limited to a measuring apparatus such as a smart wristband and a smart earphone which utilizes the present solution and in which a photoelectric pulse measuring instrument is built. The present solution may be applied to other wearable electronic products which require pulse test.

Figure 10:
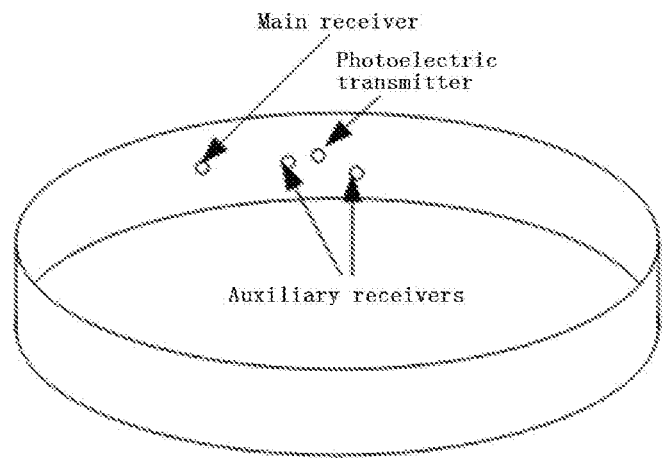
FIG. 10 is a schematic view of another smart wristband according to an embodiment of the present disclosure.

FIG. 10 is a schematic view of a smart wristband according to an embodiment of the present disclosure. As shown in FIG. 10, the smart wristband is provided with an photoelectric transmitter and three photoelectric receivers including one main receiver and two auxiliary receivers, wherein the photoelectric transmitter and the three photoelectric receivers are all arranged on inside where the smart wristband contacts with wrist skin, the main receiver is arranged at a position farther from the photoelectric transmitter, the two auxiliary receivers are arranged at a position closer to the photoelectric transmitter. When the user is duly wearing the wristband to measure the pulse, at least one artery is located between the main receiver and the photoelectric transmitter, and no artery passes between the two auxiliary receivers and the photoelectric transmitter.

Figure 11:
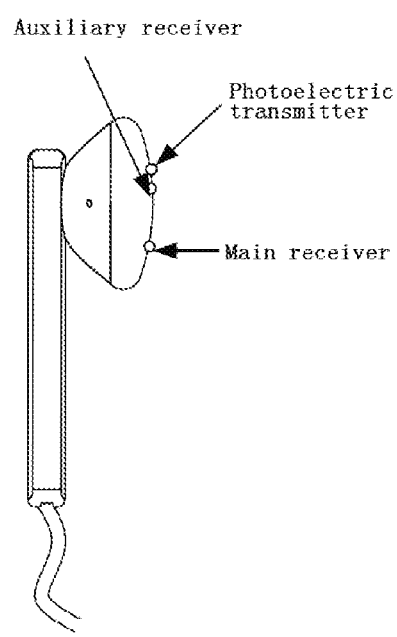
FIG. 11 is a schematic view of another smart earphone according to an embodiment of the present disclosure.

FIG. 11 is a schematic view of a smart earphone according to an embodiment of the present disclosure. As shown in FIG. 11, the smart earphone is provided with a photoelectrical transmitter and two photoelectric receivers including one main receiver and one auxiliary receiver, wherein the photoelectric transmitter and the two photoelectric receivers are arranged at a position on an earplug contacting with ear skin, the main receiver is arranged a position farther away from the photoelectric transmitter, the auxiliary receivers are closer to the photoelectric transmitter. When the user is duly wearing the earphone to measure the pulse, at least one artery is located between the main receiver and the photoelectric transmitter, and no artery passes between the auxiliary receivers and the photoelectric transmitter.

Step S920: based on at least one auxiliary-path light signal, adaptively filtering the motion interference in the main-path light signal and obtaining an adaptive filtration result.

Specifically, the adaptive filtering operation in step S920 may comprise a plurality of adaptive filtering cycles, operation of each adaptive filtering cycle comprising:

Obtaining a fitting filter of each auxiliary-path light signal according to light intensity relationship between the reflected light in each auxiliary-path light signal and the reflected light in the main-path light signal; in one adaptive filtering cycle, calculating output signals of the auxiliary-path light signals passing through respective fitting filters; subtracting output signals of the auxiliary-path light signals from the main-path light signal to obtain a filtration result output in this adaptive filtering cycle.

After a filtration result output in this adaptive filtering cycle is obtained, said step S920 may further comprise:

calculating an update amount of fitting filter coefficients of each auxiliary-path light signal according to a relevant function of the filtration result in this adaptive filtering cycle and each auxiliary-path light signal; adding the update amount correspondingly to the fitting filter coefficients of each auxiliary-path light signal, and updating the fitting filters of the auxiliary-path light signals to obtain fitting filters of the auxiliary-path light signals in next adaptive filtering cycle.

After updating the fitting filters of the auxiliary-path light signals in each adaptive filtering cycle, the step S920 may further comprise:

judging whether the updated fitting filter satisfies a filter constraint condition, taking the updated fitting filter as a fitting filter of the auxiliary-path light signal in next adaptive filtering cycle if the updated fitting filter satisfies the filter constraint condition, and performing normalization processing for the updated fitting filter if the updated fitting filter does not satisfy the filter constraint condition, and taking the normalized fitting filter as a fitting filter of the auxiliary-path light signal in next adaptive filtering cycle.

When calculating that the update amount of the fitting filter coefficients of an auxiliary-path light signal is smaller than an update threshold, confirming that the auxiliary receiver achieves accurate tracing of the user's motions.

Step S930: extracting a pulse signal from the adaptive filtration result.

After the processing in the step S920, among the adaptive filtration result obtained by adaptively filtering motion interference signals from the main-path light signal, most signals are signals relevant to the pulse signal, and the pulse signal may be extracted therefrom to perform ECG analysis.

According to the photoelectric type pulse signal measuring method according to the embodiment of the present disclosure, the photoelectric sensor array technology is utilized, the motion interference signal is adaptively filtered from the main-path light signal, the contact degree between the apparatus and skin is not limited rigidly, and the motion interference upon the photoelectric type pulse signal measurement can be eliminated simply and effectively. The method according to the embodiment of the present disclosure is adapted to be used on a wearable product.

In a preferred embodiment, the auxiliary-path light signals and the main-path light signal are pre-processed before the motion interference is adaptively filtered from the main-path light signal based on the auxiliary-path light signals. The pre-processed content comprises:

performing logarithmic operation processing for the main-path light signal and auxiliary-path light signals; and filtering a direct current component and a high-frequency component from the main-path light signal and auxiliary-path light signals respectively after the logarithmic operation processing.

The function of the pre-processing is to perform logarithmic operation and blocking operation for the signal of the photoelectric receiver, and such operations may be completed by a pre-processor in practice.

After the above pre-processing, other motion interference irrelevant to heartbeat, for example motion interference affecting the pulse signal measurement such as breath or micro-motion, can be removed from the main-path light signal and auxiliary-path light signals, thereby accurately obtaining an adaptive filtration result after the motion interference is eliminated.

Noticeably, if after the main-path light signal and auxiliary-path light signals are subjected to the above pre-processing, the motion interference is adaptively filtered from the main-path light signal based on the auxiliary-path light signals to obtain the adaptive filtration result, the extracting a pulse signal from the adaptive filtration result in step S930 comprises: performing exponential operation processing for the adaptive filtration result; extracting the pulse signal from a result after the exponential operation processing.

Figure 12:
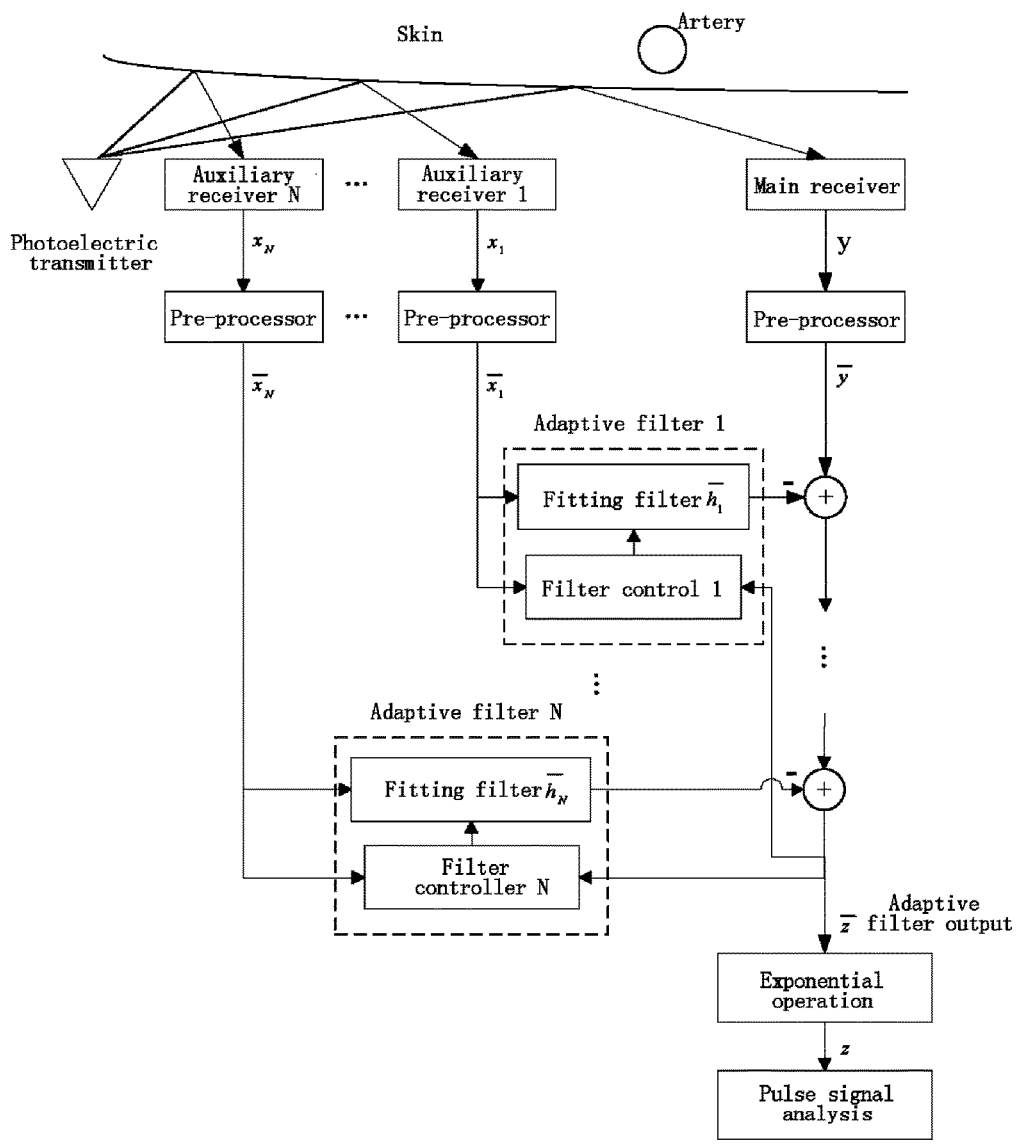
FIG. 12 is a schematic view of another photoelectric sensor array signal processing structure according to an embodiment of the present disclosure.

The principle of the photoelectric type pulse signal measuring method according to an embodiment of the present disclosure is illustrated in conjunction with FIG. 12. FIG. 12 is a schematic view of another photoelectric sensor array signal processing structure according to an embodiment of the present disclosure.

Referring to FIG. 12, the photoelectric sensor array comprises a plurality of photoelectric receivers and a photoelectric transmitter, wherein the photoelectric receivers comprise one main receiver and a plurality of auxiliary receivers. The light beam transmitted by the photoelectric transmitter is irradiated on skin, the main receiver is used to receive the light signal reflected back from a surface of skin having an artery underneath, components of the signal comprise pulse signal and motion interference, N auxiliary receivers are used to receive a signal reflected back from a surface of skin without any artery underneath (an artery-less area), their signals substantially only include motion interference component. Upon application to the photoelectric type pulse signal measuring apparatus, when the user duly wears the measuring apparatus, the main receiver and the photoelectric transmitter are arranged at a specified position closer to the skin, and at least one artery passes between the main receiver and the photoelectric transmitter. The auxiliary receivers are nearer away from the photoelectric transmitter, and no artery passes between the auxiliary receives and the photoelectric transmitter.

After the signal of the main receiver and the signals of the N auxiliary receivers all go through the pre-processing, the pre-processed signals of the auxiliary receivers go through the adaptive filter to eliminate the motion interference from the pre-processed signal of the main photoelectric receiver. The output signal after the motion interference is eliminated from the main receiver signal may be used for pulse signal analysis and extraction.

To enable adaptive filtration of the motion interference from the main-path light signal, the solution of the present disclosure is divided into several basic parts: pre-processor and adaptive filter, wherein the adaptive filter of each auxiliary receiver comprises a fitting filter and a filter controller. What is received by the photoelectric receiver is light intensity signal, signals y, $x_1$, $x_2$, ..., $x_N$ of the main and auxiliary receivers are respectively input into corresponding pre-processors for processing. The main and auxiliary receiver signals output by the pre-processors are $\bar{y}$, $\bar{x}_1$, $\bar{x}_2$, ..., $\bar{x}_N$. The outputs $\bar{x}_1$, $\bar{x}_2$, ..., $\bar{x}_N$ of the pre-processors corresponding to the auxiliary receivers are respectively input into the adaptive filter of each auxiliary receiver. The motion interference in the main receiver signal $\bar{y}$ after the pre-processing is eliminated by using a result after the signals $\bar{x}_1$, $\bar{x}_2$, ..., $\bar{x}_N$ from the auxiliary receivers go through adaptive filtration. In the output signal z after the adaptive filtration, most of the motion interference is eliminated, and the signal output after the filtration is chiefly the pulse signal.

When skin and the photoelectric pulse measuring instrument are stationary relative to each other, the light signal transmitted by the photoelectric transmitter is reflected on the skin surface, transmitted, then received by the main receiver. The present embodiment uses Lambert-Beer law to obtain the following formula:

$$y = I e^{-\epsilon d_0}$$

Wherein I is light source intensity of the photoelectric transmitter, $\epsilon$ is a reflection coefficient of the skin and subcutaneous tissue for light, $d_0$ is a length of a light transmission pathway, and y is a signal of the main receiver. Since the subcutaneous artery's absorption and reflection of light energy varies with pulse, that is, a reflectivity $\epsilon$ varies with the pulse, and the light intensity of the reflected light also varies with the pulse.

Figure 13:
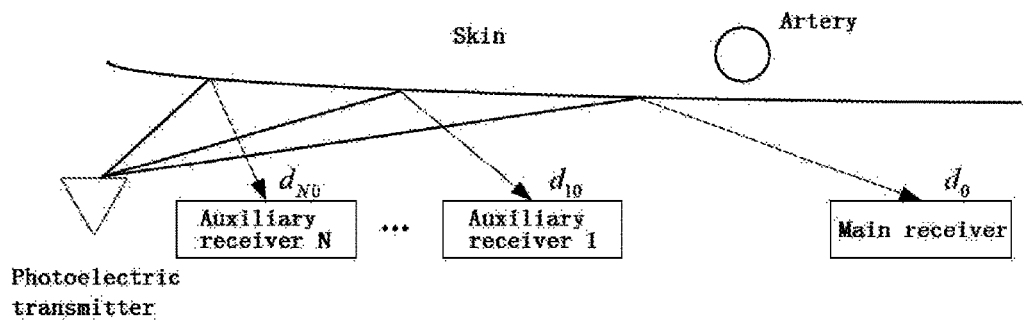
FIG. 13 is a schematic view of an optical transmission path when there is no motion according to an embodiment of the present disclosure.

As shown in FIG. 13, FIG. 13 is a schematic view of an optical transmission path when there is no motion according to an embodiment of the present disclosure. When the skin and the measuring apparatus provided by the solution are stationary relative to each other, what is carried by the signal y of the main receiver may be taken as totally light intensity signal of the pulse signal $y_P$. Therefore, there is the following:

$$y_P = Ie^{-\epsilon d_0}.$$

Figure 14:
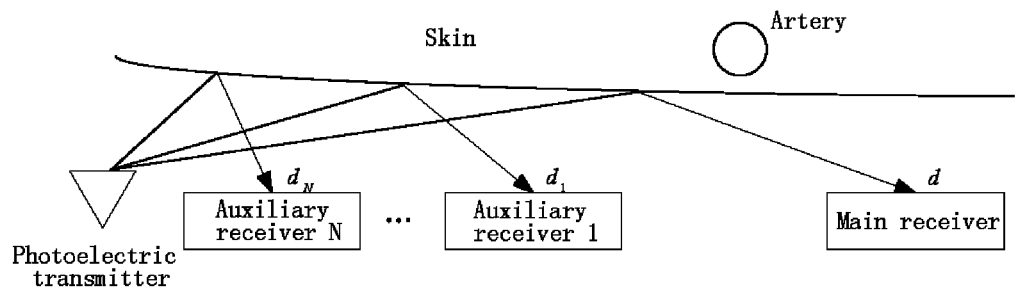
FIG. 14 is a schematic view of an optical transmission path when there is a motion according to an embodiment of the present disclosure.

In practical use, as shown in FIG. 14, FIG. 14 is a schematic view of an optical transmission path when there is a motion according to an embodiment of the present disclosure. The skin and the measuring apparatus provided by the solution move relative to each other. When the relative positions of the two change, the length of the light transmission pathway also changes, and the signal y of the main receiver also changes. The signal y of the main receiver is divided into two parts: one part is light intensity signal $y_P$ carrying pulse information (light signal transmitted by the light transmitter, reflected by the skin surface and received by the main receiver), and the other part is transmission path function $y_A$.

When the length of the light transmission pathway becomes d, the signal of the main receiver will become $$y = Ie^{-\epsilon d}$$

If the length of the light transmission pathway changes, the transmission path function may be represented as the following:

$$y_A = e^{-\epsilon(d-d_0)}$$

The signal y of the main receiver is a product of the pulse signal $y_P$ and the transmission path function $y_A$, and may be expressed as follows:

$$y = y_P y_A$$

$$y_A = e^{-\epsilon \Delta d}$$

wherein $\Delta d = d - d_0$ when a distance between the photoelectric pulse measuring instrument and skin is fixed, the length of the light transmission pathway is a constant $d_0$; when there is no relative motion, the transmission path function $y_A$ is a constant.

The signal of the auxiliary receiver does not include pulse signal component or only includes extremely little pulse signal component, the skin-reflected light is closer to the auxiliary receiver, and there is no artery around. Hence, the pulse signal does not reach the auxiliary receiver, and the pulse signal received by the auxiliary receiver may be neglected. Upon taking one auxiliary receiver k in an auxiliary receiver group, a photoelectric signal $x_k$ received by the auxiliary receiver may be expressed as follows:

$$x_k = Ie^{-\epsilon_0 d_k}$$

Wherein I is light source intensity of the photoelectric transmitter, $\epsilon_0$ is a reflectivity of the skin surface without artery underneath to light, and $d_k$ is a transmission path length of light from the photoelectric transmitter to the auxiliary receiver k. When there is no relative motion, transmission path length from the photoelectric transmitter to the auxiliary receiver k is $d_{k0}$, $x_k$ is a constant and set as $x_{k0}$.

When there is a relative motion and the transmission path changes, the photoelectric signal received by the auxiliary receiver includes:

$$x_k = Ie^{-\epsilon_0 d_k}$$
$$= x_{k0} e^{-\epsilon_0 (d_k - d_{k0})}$$

Wherein $d_{k0}$ is a transmission attenuation factor of light intensity at a per unit transmission distance and approximately a constant, $d_k$ is a change quantity of the light transmission path length and is a variable of sampling time n.

Therefore, there is the following equation:

$$x_k = x_{k0} e^{-\epsilon_0 \Delta d_k}$$

wherein $$\Delta d_k = d_k - d_{k0}$$

When the distance between the auxiliary receiver and main receiver is not too far, flexible deformation of the wearable apparatus is small, and a geometric dimension of the apparatus almost does not change. Taking this, in the present embodiment, the path change quantities of the auxiliary receivers and main receiver relative to skin are in a relation of linear transfer function.

$$\Delta d = \sum_{k=1}^{N} h_k * \Delta d_k$$

It may be inferred from the y and $x_k$ expression formula that if logarithm is solved for y and $x_k$, there will be:

$$\ln y = -\epsilon \Delta d + \ln y_P$$

$$\ln x_k = -\epsilon_0 \Delta d_k + \ln x_{k0}$$

Since $x_{k0}$ is a constant, its logarithm function value $\ln x_{k0}$ may be removed through the blocking operation of the pre-processing. Again, according to the relationship of $\Delta d$ and $\Delta d_k$, there may be:

$$\bar{y} = \ln y$$
$$= -\epsilon \Delta d + \ln y_P$$
$$\bar{x}_k = -\epsilon_0 \Delta d_k$$

$\bar{x}_k$ and $\bar{y}$ are both known, and $\epsilon_0$ is a constant value. If the relationship of $-\epsilon \Delta d$ and $\Delta d_k$ can be estimated, $-\epsilon \Delta d$ is removed from $\bar{y}$, $\ln y_P$ may be solved, and thereby exponential operation is performed to solve the pulse signal $y_P$. $\Delta d$ and $\Delta d_k$ are in a linear relationship, $$\Delta d = \sum_{k=1}^{N} h_k * \Delta d_k$$

In a wearable apparatus, since the wearing manner might change at any time, $h_k$ is caused to change, and meanwhile $\epsilon$ also time-varies. It may be believed that $-\epsilon \Delta d$ and $\Delta d_k$ are in a time-varying linear relationship.

That is, $$-\varepsilon \Delta d = \sum_{k=1}^{N} -\varepsilon h_k * \Delta d_k$$

$$= \sum_{k=1}^{N} -\frac{\varepsilon}{\varepsilon_0} h_k * \bar{x}_k$$

$$= \sum_{k=1}^{N} \bar{h}_k * \bar{x}_k$$

Wherein $$\bar{h}_k = -\frac{\varepsilon}{\varepsilon_0} h_k$$

A reasonable manner is allowing $\bar{h}_k$ to adaptively change with the environment, and the order length of filter $\bar{h}_k$ estimated using adaptive filtering manner is related to a sampling frequency. When the sampling frequency rises, the order length will rise. Generally, when the sampling frequency is 100 Hz, the order length may be the fifth order; when the sampling frequency is doubled and becomes 200 Hz, the order length is also doubled and become the 10$^{th}$ order.

In each operation cycle, a new signal enters the main and auxiliary receivers, after a procedure of pre-processing filtering, and filter updating, the adaptive filtration result is the pulse signal, and output to a subsequent level for pulse analysis.

Still referring to FIG. 12, specific implementation modes of the pre-processor and adaptive filter are as follows:

1. Pre-processor

The pre-processor functions to perform logarithmic operation and blocking operation for the signal of the photoelectric receiver.

The logarithmic operation is to solve a natural logarithm for the light intensity signal and may be performed by using a logarithmic device.

The blocking operation is to filter the direct current component and high-frequency component in the light intensity signal, and may be performed by using a blocking filter.

The pre-processor may be taken as a cascading combination of the logarithmic device and blocking filter. The logarithmic device solves a natural logarithm for the light intensity signal. The blocking filter is a bandpass filter. A lower cutoff frequency of the bandpass filter is generally much lower than a healthy adult's heartbeat frequency, e.g., 0.1 Hz may be adopted, and an upper cutoff frequency is generally much higher than a healthy adult's heartbeat frequency, e.g., 10 Hz may be adopted.

2. Adaptive Filter

The adaptive filter is used to remove a signal component in the main receiver signal similar to the motion interference, and may be divided into two portions: a fitting filter and a filter controller.

The fitting filter is used to estimate a fitting relationship $\bar{h}$ of a light signal of the reflected light reaching the auxiliary receiver and a light signal of the reflected light reaching the main receiver, that is to say, the fitting filter of each auxiliary-path light signal is obtained according to the light intensity change tendency of the reflected light in each auxiliary-path light signal and the main-path light signal. The fitting filter obtains the fitting filter of the light signal of the reflected light reaching each auxiliary receiver and the light signal of the reflected light reaching the main receiver according to the light intensity relationship of the reflected light in each auxiliary-path light signal and in the main-path light signal.

In an adaptive filtering cycle, output signal of the auxiliary-path light signals after undergoing corresponding fitting filters are calculated; the output signals of the auxiliary-path light signals are subtracted from the main-path light signal to obtain a filtering result $\bar{z}$ output under this adaptive filtering cycle.

The filter controller is used to calculate a relevant function of the $\bar{z}$ signal and the signal $\bar{x}_k$ of each auxiliary receiver, that is to say, an update amount of fitting filter coefficients of each auxiliary-path light signal is calculated according to a relevant function of the filtration result in this adaptive filtering cycle and each auxiliary-path light signal (signal $\bar{x}_k$ of each auxiliary-path light signal undergoing the pre-processing). In this way, a proportion of the motion interference in the $\bar{z}$ signal can be determined to adjust the update amount of the fitting filter of each auxiliary receiver. Optionally, the above relevant function may also be a relevant function of the filtration result in this adaptive filtering cycle and the signal of each auxiliary-path light signal undergoing the fitting filter.

Regarding the fitting filter $h_k$ of the $k^{th}$ auxiliary receiver, assume that its order length is L, its update amount $\Delta h_k$ is calculated in the following manner $$\Delta \bar{h}_k(l) = \frac{\bar{x}_k(n-l+1)\bar{z}(n)}{E(\bar{x}_k^2)},$$

$$L \geq l \geq 1$$

The update amount is added correspondingly to the fitting filter coefficients of each auxiliary-path light signal, and the fitting filters of the auxiliary-path light signals are updated to obtain the fitting filters of the auxiliary-path light signals in next adaptive filtering cycle. That is, the original filter is added with the update amount to obtain a new filter, which can be expressed by the following equation:

$$\bar{h}_k(l)_{new} = \bar{h}_k(l)_{old} + \Delta \bar{h}_k(l)$$

Hereunder, illustration is presented still in combination with FIG. 12:

The pre-processed signals of the auxiliary receivers pass through the fitting filters, and are subtracted one by one from the pre-processed main receiver signal to obtain an adaptive filter output signal $\bar{z}$ under an adaptive filtering cycle. Specifically, Assume that the fitting filter of the $k^{th}$ auxiliary receiver is $h_k$, and n is a sampling serial number of the digital signal, the output $\bar{z}$ may be represented as follows:

$$\bar{z}(n) = \bar{y}(n) - \sum_{k=1}^{M} \bar{x}_k(n) * \bar{h}_k(n)$$

$\bar{z}$ is the adaptive filtration result. After $\bar{z}$ is subjected to exponential operation, it is restored to obtain signal z:

$$z = \exp(\bar{z})$$

The pulse signal is extracted from the signal z and may be transmitted to next level for pulse signal analysis.

Since the pulse signal analysis solution has a certain fault tolerance, in a processing manner of the present embodiment, the adaptive filtration result obtained under each adaptive filter cycle is output in real time to facilitate subsequent pulse signal analysis and processing.

After the fitting filters of the auxiliary-path light signals are updated, judgment is made as to whether the updated fitting filters satisfy a filter constraint condition. The updated fitting filter is taken as a fitting filter of the auxiliary-path light signal in next adaptive filtering cycle if the updated fitting filter satisfies the filter constraint condition, and normalization processing for the updated fitting filter is performed if the updated fitting filter does not satisfy the filter constraint condition, and the normalized fitting filter is taken as a fitting filter of the auxiliary-path light signal in next adaptive filtering cycle. The reason is as follows:

Since there is only skin surface reflection and there is no artery absorption between the auxiliary receiver and the photoelectric transmitter, the reflectivity $\epsilon_0$ is generally obviously greater than $\epsilon$, and $$\frac{\varepsilon}{\varepsilon_0}$$

is smaller than 1. Hence, $$\sum_{l=1}^{L} \overline{h}_k^2(l) < 1.$$

Therefore, the present embodiment employs the filter constraint condition that a sum of squares of the fitting filter coefficients is smaller than 1, to perform filter constraint for the solved fitting filters. When the sum of squares of the coefficients of the filter is greater than 1, normalization processing needs to be performed for the filter. The normalization processing formula may be represented as follows:

$$h_k = h_k \Bigg/ \max\left(1, \sqrt{\sum_{l=1}^{L} h_k^2(l)}\right)$$

The fitting filers of all auxiliary receivers are updated in turn by this method. The flow proceeds to next adaptive operation cycle upon completion of update of the fitting filers of all auxiliary receivers.

Figure 15:
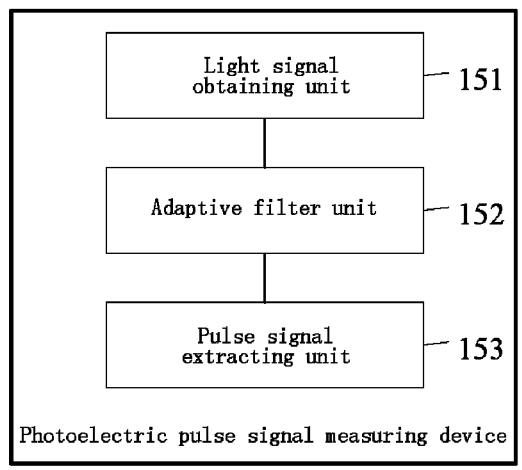
FIG. 15 is a block diagram of a photoelectric type pulse signal measuring device according to an embodiment of the present disclosure.

According to another aspect, the present disclosure further provides a photoelectric type pulse signal measuring device. FIG. 15 is a block diagram of a photoelectric type pulse signal measuring device according to an embodiment of the present disclosure. Referring to FIG. 15, the apparatus comprises a light signal obtaining unit 151, an adaptive filter unit 152 and a pulse signal extracting unit 153.

The light signal obtaining unit 151 is configured to obtain a main-path light signal transmitted by a photoelectric transmitter and reflected back from a surface of skin having an artery underneath, and obtain at least one auxiliary-path light signal transmitted by the same photoelectric transmitter and reflected back from a surface of skin without any artery underneath.

The adaptive filter unit 152 is configured to, based on at least one auxiliary-path light signal, adaptively filter the motion interference in the main-path light signal and obtain an adaptive filtration result.

The pulse signal extracting unit 153 is configured to extract a pulse signal from the adaptive filtration result.

According to the photoelectric type pulse signal measuring device according to the embodiment of the present disclosure, the photoelectric sensor array technology is utilized, the motion interference signal is adaptively filtered from the main-path light signal, the contact degree between the apparatus and skin is not limited rigidly, and the motion interference upon the photoelectric type pulse signal measurement can be eliminated simply and effectively.

In a preferred embodiment, before the motion interference is adaptively filtered by the adaptive filter unit from the main-path light signal, the auxiliary-path light signals and the main-path light signal are pre-processed to filter other motion interference irrelevant to heartbeat, for example motion interference affecting the pulse signal measurement such as breath or micro-motion, from the main-path light signal and auxiliary-path light signals, and then the main-path light signal and auxiliary-path light signals after having gone through the above pre-processing are transmitted to the adaptive filter unit to filter the motion interference in the main-path light signal, the obtained adaptive filtration result is subjected to the exponential operation processing to extract the pulse signal from the result after the exponential operation processing.

Figure 16:
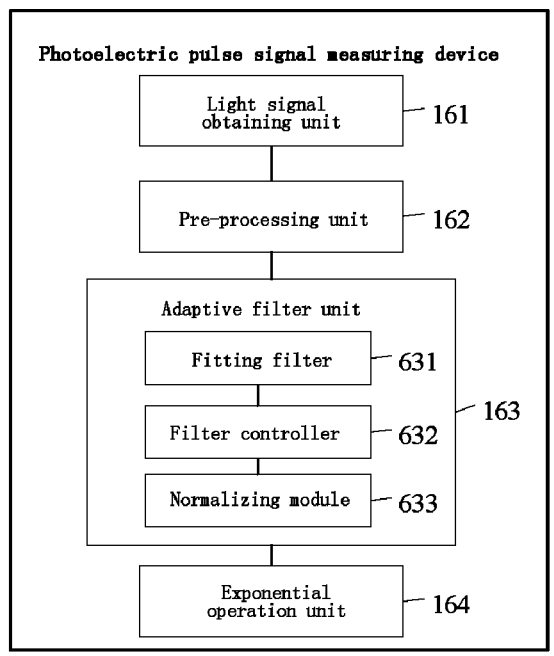
FIG. 16 is a block diagram of another photoelectric type pulse signal measuring device according to an embodiment of the present disclosure.

Specifically, referring to FIG. 16, FIG. 16 is a block diagram of another photoelectric type pulse signal measuring device according to an embodiment of the present disclosure. The photoelectric type pulse signal measuring device comprises: a light signal obtaining unit 161, a pre-processing unit 162, an adaptive filter unit 163 and an exponential operation unit 164.

The light signal obtaining unit 161 is configured to obtain a main-path light signal transmitted by a photoelectric transmitter and reflected back from a surface of skin having an artery underneath, and obtain at least one auxiliary-path light signal transmitted by the same photoelectric transmitter and reflected back from a surface of skin without any artery underneath.

The pre-processing unit 162 is configured to perform logarithmic operation processing for the main-path light signal and auxiliary-path light signals; and filter a direct current component and a high-frequency component from the main-path light signal and auxiliary-path light signals respectively after the logarithmic operation processing.

The adaptive filter unit 163 is configured to, based on the at least one auxiliary-path light signal, adaptively filter the motion interference in the main-path light signal, and obtain an adaptive filtration result.

Specifically, the adaptive filter unit 163 comprises:

a fitting filter 631 configured to obtain the fitting filters of the auxiliary-path light signals according to light intensity relationship of reflected light in the auxiliary-path light signals and reflected light in the main-path light signal; in one adaptive filtering cycle, calculate output signals of the auxiliary-path light signals passing through respective fitting filters; subtract output signals of the auxiliary-path light signals from the main-path light signal to obtain a filtration result output in this adaptive filtering cycle.

a filter controller 632 configured to calculate an update amount of fitting filter coefficients of each auxiliary-path light signal according to a relevant function of the filtration result in this adaptive filtering cycle and each auxiliary-path light signal; add the update amount correspondingly to the fitting filter coefficients of each auxiliary-path light signal, and update the fitting filters of each auxiliary-path light signal to obtain the fitting filter of each auxiliary-path light signal in next adaptive filtering cycle.

a normalizing module 633 configured to judge whether the updated fitting filter satisfies a filter constraint condition, take the updated fitting filter as a fitting filter of the auxiliary-path light signal in next adaptive filtering cycle if the updated fitting filter satisfies the filter constraint condition, and perform normalization processing for the updated fitting filter if the updated fitting filter does not satisfy the filter constraint condition, and take the normalized fitting filter as a fitting filter of the auxiliary-path light signal in next adaptive filtering cycle.

The exponential operation unit 164 is configured to perform exponential operation processing for the adaptive filtration result and extracting the pulse signal from a result after the exponential operation processing.

In the present embodiment, the pre-processing unit performs logarithmic operation and blocking operation for the signal of the photoelectric receiver, remove other motion interference irrelevant to the heartbeat in the main-path light signal and auxiliary-path light signals, to allow for more accurate adaptive filtration result after the motion interference is adaptively filtered from the main-path light signal.

According to a further aspect, embodiments of the present disclosure further provide a measuring apparatus, comprising the above-mentioned photoelectric type pulse signal measuring device.

The measuring apparatus is provided with a photoelectric transmitter and two or more photoelectric receivers, wherein one photoelectric receiver is a main receiver and the remaining photoelectric receivers are auxiliary receivers.

When the user wears the measuring apparatus to measure the pulse signal, the main receiver and the photoelectric transmitter are placed at a specified position of the skin, at least one artery passes between the main receiver and the photoelectric transmitter, and no artery passes between the auxiliary receivers and the photoelectrical transmitter.

In practical use, the measuring apparatus is preferably an annular apparatus adapted to a human wrist, wherein the photoelectric transmitter and the photoelectric receivers are arranged on inside where the annular apparatus contacts with the wrist skin. Certainly, the measuring apparatus may also be an earphone. The photoelectric transmitter and the photoelectric receivers are arranged at a position on an earplug contacting with ear skin. The present technical solution exemplarily provides the above two types of measuring apparatus. Noticeably, the present disclosure by no means limits the designed structure of the measuring apparatus so long as the photoelectric sensor array technology can be used to perform corresponding adaptive filter processing for the signals of the photoelectric transmitter and photoelectric receivers so as to eliminate the motion interference upon photoelectric type pulse signal measurement, and improve the precision of the pulse signal detection.

To conclude, embodiments of the present disclosure provide a photoelectric type pulse signal measuring method and apparatus. Based on a light propagation model and physical characteristics of light intensity signal, by using photoelectric sensor array technology, obtain a main-path light signal transmitted by a photoelectric transmitter and reflected back from a surface of skin having an artery underneath, obtain at least one auxiliary-path light signal receiving an ambient light signal, and then based on the auxiliary-path light signal, adaptively filter the ambient light interference signal from the main-path light signal so as to eliminate or reduce ambient light interference upon photoelectric detection of the pulse signal and improve the precision of pulse signal detection. Alternatively, obtain a main-path light signal transmitted by a photoelectric transmitter and reflected back from a surface of skin having an artery underneath, obtain at least one auxiliary-path light signal transmitted by the same photoelectric transmitter and reflected back from a surface of skin without any artery underneath, and then based on the auxiliary-path light signal, adaptively filter the motion interference signal from the main-path light signal so as to eliminate or reduce the motion interference upon photoelectric detection of the pulse signal and improve the precision of pulse signal measurement. By using the photoelectric array to adaptively remove the ambient light interference or motion interference from the photoelectric signal without need to rigidly limit the contact degree of the apparatus and skin, the present technical solution can simply and effectively eliminate the ambient light interference or motion interference upon photoelectric pulse signal measurement. In addition, the present solution does not require high-intensity light source, and can reduce the power consumption of the measuring apparatus, and prolong the service life. Meanwhile, the input to be processed by the present solution is the photoelectric signal of the same type, and may be implemented by using the same signal sampling system and sampling cycle, thereby simplifying the complexity of the measuring system and substantially reducing data operation quantity. Furthermore, in a preferred solution, pre-processing is performed for the main-path light signal and auxiliary-path light signals, to filter a direct current component and a high-frequency component from the main-path light signal and auxiliary-path light signals, and perform frequency energy equalization related to the pulse signal respectively for the main-path light signal and auxiliary-path light signals from which the direct current component and high-frequency component are already filtered, thereby obtaining an adaptive filtration result after the ambient light interference is removed more accurately. Optionally, in a preferred solution, pre-processing is performed for the main-path light signal and auxiliary-path light signals respectively, to perform logarithmic operation and blocking operation for the signal of the photoelectric receiver, other motion interference irrelevant to the heartbeat is removed from the main-path light signal and auxiliary-path light signals, to accurately obtain adaptive filtration result after the motion interference is eliminated.

What are stated above are only preferred embodiments of the present disclosure and not used to limit the protection scope of the present disclosure. Any modifications, equivalent substitutions and improvement within the spirit and principle of the present disclosure are all included in the protection scope of the present disclosure.

What is claimed is:

1. A photoelectric type pulse signal measuring method, wherein the method comprises:
   obtaining a main-path light signal transmitted by a photoelectric transmitter and reflected back from a surface of skin having an artery underneath, and obtaining at least one auxiliary-path light signal for receiving an ambient light signal;
   by using the at least one auxiliary-path light signal, adaptively filtering ambient light interference from the main-path light signal and obtaining an adaptive filtration result; and
   extracting a pulse signal from the adaptive filtration result;
   wherein obtaining the main-path light signal and obtaining the at least one auxiliary-path light signal comprises:
   providing a wearable measuring apparatus with only one photoelectric transmitter and two or more photoelectric receivers, wherein one of the photoelectric receivers is a main receiver, wherein the remaining photoelectric receiver(s) is(are) auxiliary receiver(s), and wherein the auxiliary receiver(s) comprise(s) an ambient light auxiliary receiver;

placing the main receiver and the photoelectric transmitter at a specified position of the skin respectively so that at least one artery passes between the main receiver and the photoelectric transmitter, the ambient light auxiliary receiver(s) facing toward an external environment, a distance between each ambient light auxiliary receiver and the photoelectric transmitter being larger than a distance threshold so that reflected light generated by the photoelectric transmitter does not enter the ambient light auxiliary receiver;

using the main receiver to receive the light signal transmitted by the photoelectric transmitter and reflected back from the surface of skin having an artery underneath; and using the ambient light auxiliary receiver(s) to receive the ambient light signal;

wherein adaptively filtering ambient light interference from the main-path light signal comprises:

obtaining a transmission path filter of each auxiliary-path light signal according to a light intensity relationship between ambient light in the auxiliary-path light signal and ambient light in the main-path light signal;

in one adaptive filtering cycle, calculating an output signal of each auxiliary-path light signal passing through respective transmission path filter;

subtracting the output signal of each auxiliary-path light signal from the main-path light signal to obtain a filtration result output in this adaptive filtering cycle;

calculating an update amount of transmission path filter coefficients of each auxiliary-path light signal according to a relevant function of the filtration result in this adaptive filtering cycle and the auxiliary-path light signal; and adding the update amount correspondingly to the transmission path filter coefficients of each auxiliary-path light signal, to update the transmission path filter of the auxiliary-path light signal and to obtain a transmission path filter of the auxiliary-path light signal in next adaptive filtering cycle.

2. The method according to claim 1, wherein before adaptively filtering ambient light interference from the main-path light signal, the method further comprises:

filtering a direct current component and a high-frequency component from the main-path light signal and the at least one auxiliary-path light signal; and performing frequency energy equalization related to the pulse signal respectively for the main-path light signal and the at least one auxiliary-path light signal from which the direct current component and high-frequency component are already filtered.

3. The method according to claim 1, wherein after updating the transmission path filter of each auxiliary-path light signal, the method further comprises:

judging whether an updated transmission path filter satisfies a filter constraint condition, and if yes, taking the updated transmission path filter as a transmission path filter of the auxiliary-path light signal in next adaptive filtering cycle, and if not, performing normalization processing for the updated transmission path filter, and taking the normalized transmission path filter as a transmission path filter of the auxiliary-path light signal in next adaptive filtering cycle.

4. The method according to claim 1, wherein providing the wearable measuring apparatus includes providing the wearable measuring apparatus with three or more photoelectric receivers, wherein one of the auxiliary receivers includes a motion auxiliary receiver, and wherein the motion auxiliary receiver is used to receive an auxiliary-path light signal reflected back from a surface of skin without any artery underneath; the method further comprising:

obtaining the at least one auxiliary-path light signal transmitted by the photoelectric transmitter and reflected back from a surface of skin without any artery underneath; and by using the at least one auxiliary-path light signal, adaptively filtering ambient light interference and motion interference from the main-path light signal to obtain the adaptive filtration result.

5. The method according to claim 4, wherein adaptively filtering ambient light interference and motion interference from the main-path light signal to obtain the adaptive filtration result comprises:

performing a first pre-processing for the auxiliary-path light signal for receiving the ambient light signal to filter a direct current component and a high-frequency component;

adaptively filtering the ambient light interference from the main-path light signal by using the auxiliary-path light signal after the first pre-processing to obtain a first-level adaptive filtering output signal;

performing a second pre-processing respectively for the auxiliary-path light signal reflected back from the surface of skin without any artery underneath and the first-level adaptive filtering output signal to filter a direct current component and a high-frequency component; and by using the auxiliary-path light signal after the second pre-processing, adaptively filtering the motion interference from the first-level adaptive filtering output signal after the second pre-processing to obtain a second-level adaptive filtering output signal as the adaptive filtration result.

6. A photoelectric type pulse signal measuring method, wherein the method comprises:

obtaining a main-path light signal transmitted by a photoelectric transmitter and reflected back from a surface of skin having an artery underneath, and obtaining at least one auxiliary-path light signal transmitted by the photoelectric transmitter and reflected back from a surface of skin without any artery underneath;

by using the at least one auxiliary-path light signal, adaptively filtering motion interference from the main-path light signal to obtain an adaptive filtration result; and extracting a pulse signal from the adaptive filtration result;

wherein obtaining the main-path light signal and obtaining the at least one auxiliary-path light signal comprises:

providing a wearable measuring apparatus with only one photoelectric transmitter and two or more photoelectric receivers, wherein one of the photoelectric receivers is a main receiver and the remaining photoelectric receiver(s) is(are) auxiliary receiver(s);

placing the main receiver and the photoelectric transmitter at a specified position of skin respectively so that at least one artery passes between the main receiver and the photoelectric transmitter, and no artery passes between any auxiliary receiver and the photoelectric transmitter;

using the main receiver to receive the light signal transmitted by the photoelectric transmitter and reflected back from the surface of skin having an artery underneath; and using the auxiliary receiver(s) to receive the light signal reflected back from the surface of skin without any artery underneath;

wherein adaptively filtering ambient motion interference from the main-path light signal comprises:

obtaining a fitting filter of each auxiliary-path light signal according to a light intensity relationship of reflected light in the auxiliary-path light signal and reflected light in the main-path light signal;

in one adaptive filtering cycle, calculating an output signal of each auxiliary-path light signal passing through respective fitting filter;

subtracting the output signal of the auxiliary-path light signal from the main-path light signal to obtain a filtration result output in this adaptive filtering cycle;

calculating an update amount of fitting filter coefficients of each auxiliary-path light signal according to a relevant function of the filtration result in this adaptive filtering cycle and the auxiliary-path light signal; and adding the update amount correspondingly to the fitting filter coefficients of each auxiliary-path light signal to update the fitting filter of the auxiliary-path light signal and to obtain a fitting filter of the auxiliary-path light signal in next adaptive filtering cycle.

7. The method according to claim 6, wherein before adaptively filtering motion interference from the main-path light signal, the method further comprises:

performing logarithmic operation processing for the main-path light signal and each auxiliary-path light signal respectively and filtering a direct current component and a high-frequency component from the main-path light signal and each auxiliary-path light signal respectively after the logarithmic operation processing; and wherein extracting the pulse signal from the adaptive filtration result comprises:

performing exponential operation processing for the adaptive filtration result; and extracting the pulse signal from a result of the exponential operation processing.

8. The method according to claim 6, wherein adaptively filtering motion interference from the main-path light signal comprises:

obtaining a fitting filter of each auxiliary-path light signal according to a light intensity relationship between reflected light in the auxiliary-path light signal and reflected light in the main-path light signal;

in one adaptive filtering cycle, calculating an output signal of each auxiliary-path light signal passing through respective fitting filter;

subtracting the output signal of each auxiliary-path light signal from the main-path light signal to obtain a filtration result output in this adaptive filtering cycle;

calculating an update amount of fitting filter coefficients of each auxiliary-path light signal according to a relevant function of the filtration result in this adaptive filtering cycle and the auxiliary-path light signal;

adding the update amount correspondingly to the fitting filter coefficients of each auxiliary-path light signal, to update the fitting filter of the auxiliary-path light signal and to obtain a fitting filter of the auxiliary-path light signal in next adaptive filtering cycle; and after updating the fitting filter of each auxiliary-path light signal, the method further comprises:

judging whether an updated fitting filter satisfies a filter constraint condition, and if yes, taking the updated fitting filter as a fitting filter of the auxiliary-path light signal in next adaptive filtering cycle, and if not, performing normalization processing for the updated fitting filter, and taking the normalized fitting filter as a fitting filter of the auxiliary-path light signal in next adaptive filtering cycle.

9. A measuring apparatus, comprising a photoelectric type pulse signal processor, only one photoelectric transmitter, and two or more photoelectric receivers, one of the photoelectric receivers including a main receiver and the remaining photoelectric receiver(s) including auxiliary receiver(s), the auxiliary receiver(s) including at least one of an ambient light auxiliary receiver and a motion auxiliary receiver;

the main receiver and the photoelectric transmitter placed at a specified position of skin respectively, at least one artery passing between the main receiver and the photoelectric transmitter, and the ambient light auxiliary receiver(s) facing toward external environment; a distance between each ambient light auxiliary receiver and the photoelectric transmitter being larger than a distance threshold so that reflected light generated by the photoelectric transmitter does not enter the ambient light auxiliary receiver; and no artery passes between any motion auxiliary receiver and the photoelectric transmitter;

the main receiver configured to obtain a main-path light signal transmitted by a photoelectric transmitter and reflected back from a surface of skin having an artery underneath, and transmit the main-path light signal to the photoelectric type pulse signal processor;

the ambient light auxiliary receiver configured to obtain the at least one auxiliary-path light signal for receiving an ambient light signal, and transmit the auxiliary-path light signal to the photoelectric type pulse signal processor;

the motion auxiliary receiver configured to obtain at least one auxiliary-path light signal transmitted by the photoelectric transmitter and reflected back from a surface of skin without any artery underneath, and transmit the auxiliary-path light signal to the photoelectric type pulse signal processor; and wherein the photoelectric type pulse signal processor is configured to obtain a main-path light signal transmitted by the photoelectric transmitter and reflected back from a surface of skin having an artery underneath, and obtain at least one auxiliary-path light signal for receiving an ambient light signal, adaptively filter ambient light interference from the main-path light signal and obtain an adaptive filtration result by using the at least one auxiliary-path light signal, and extract a pulse signal from the adaptive filtration result, and wherein when the at least one auxiliary-path light signal for receiving the ambient light signal is obtained, the photoelectric type pulse signal processor is configured to obtain a transmission path filter of each auxiliary-path light signal according to a light intensity relationship between ambient light in the auxiliary-path light signal and ambient light in the main-path light signal, in one adaptive filtering cycle, calculate an output signal of each auxiliary-path light signal passing through respective transmission path filter, subtract the output signal of each auxiliary-path light signal from the main-path light signal to obtain a filtration result output in this adaptive filtering cycle, calculate an update amount of transmission path filter coefficients of each auxiliary-path light signal according to a relevant function of the filtration result in this adaptive filtering cycle and the auxiliary-path light signal, and add the update amount correspondingly to the transmission path filter coefficients of each auxiliary-path light signal to update the transmission path filter of the auxiliary-path light signal and to obtain a transmission path filter of the auxiliary-path light signal in next adaptive filtering cycle; or wherein the photoelectric type pulse signal processor is configured to obtain a main-path light signal transmitted by the photoelectric transmitter and reflected back from a surface of skin having an artery underneath, and obtain at least one auxiliary-path light signal transmitted by the photoelectric transmitter and reflected back from a surface of skin without any artery underneath, adaptively filter motion interference from the main-path light signal to obtain an adaptive filtration result by using on the at least one auxiliary-path light signal, and extract a pulse signal from the adaptive filtration result, and wherein when the light signal obtaining unit is configured to obtain at least one auxiliary-path light signal transmitted by the photoelectric transmitter and reflected back from a surface of skin without any artery underneath, the photoelectric type pulse signal processor is configured to obtain a fitting filter of each auxiliary-path light signal according to a light intensity relationship of reflected light in the auxiliary-path light signal and reflected light in the main-path light signal, in one adaptive filtering cycle, calculate an output signal of each auxiliary-path light signal passing through respective fitting filter, subtract the output signal of the auxiliary-path light signal from the main-path light signal to obtain a filtration result output in this adaptive filtering cycle, calculate an update amount of fitting filter coefficients of each auxiliary-path light signal according to a relevant function of the filtration result in this adaptive filtering cycle and the auxiliary-path light signal, and add the update amount correspondingly to the fitting filter coefficients of each auxiliary-path light signal to update the fitting filter of the auxiliary-path light signal and to obtain a fitting filter of the auxiliary-path light signal in next adaptive filtering cycle.

10. The measuring apparatus according to claim 9, wherein the photoelectric type pulse signal processor is configured to filter a direct current component and a high-frequency component from the main-path light signal and the at least one auxiliary-path light signal, and perform frequency energy equalization related to the pulse signal respectively for the main-path light signal and the at least one auxiliary-path light signal from which the direct current component and high-frequency component are already filtered when the at least one auxiliary-path light signal is obtained; or wherein the photoelectric type pulse signal processor is configured to perform logarithmic operation processing for the main-path light signal and each auxiliary-path light signal respectively, and filter a direct current component and a high-frequency component from the main-path light signal and each auxiliary-path light signal respectively after the logarithmic operation processing when the at least one auxiliary-path light signal transmitted by the photoelectric transmitter is obtained.

11. The measuring apparatus according to claim 9, wherein the photoelectric type pulse signal processor is configured to judge whether an updated transmission path filter satisfies a filter constraint condition, and if yes, take the updated transmission path filter as a transmission path filter of the auxiliary-path light signal in next adaptive filtering cycle, and if not, perform normalization processing for the updated transmission path filter, and take the normalized transmission path filter as a transmission path filter of the auxiliary-path light signal in next adaptive filtering cycle; or wherein the photoelectric type pulse signal processor is configured to judge whether a updated fitting filter satisfies a filter constraint condition, and if yes, take the updated fitting filter as a fitting filter of the auxiliary-path light signal in next adaptive filtering cycle, and if not, perform normalization processing for the updated fitting filter, and take the normalized fitting filter as a fitting filter of the auxiliary-path light signal in next adaptive filtering cycle.

12. The measuring apparatus according to claim 9, wherein, the measuring apparatus is an annular apparatus adapted to a human wrist; when the photoelectric type pulse signal processor is configured to obtain at least one auxiliary-path light signal for receiving the ambient light signal, the photoelectric transmitter and the main receiver are arranged on an inside of the annular apparatus where the annular apparatus contacts with wrist skin, each ambient light auxiliary receiver is arranged on an outside of the annular apparatus where the annular apparatus does not contact with the wrist skin; when the photoelectric type pulse signal processor is configured to obtain at least one auxiliary-path light signal transmitted by the photoelectric transmitter and reflected back from a surface of skin without any artery underneath, the photoelectric transmitter and photoelectric receivers are all arranged on the inside of the annular apparatus where the annular apparatus contacts with the wrist skin; or the measuring apparatus is an earphone; when the photoelectric type pulse signal processor is configured to obtain at least one auxiliary-path light signal for receiving the ambient light signal, the photoelectric transmitter and the main receiver are arranged respectively at a position on an earplug contacting with ear skin, each ambient light auxiliary receiver is arranged at a position of the earplug not contacting with the ear skin; when the photoelectric type pulse signal processor is configured to obtain at least one auxiliary-path light signal transmitted by the photoelectric transmitter and reflected back from a surface of skin without any artery underneath, the photoelectric transmitter and photoelectric receivers are all arranged respectively at a position on an earplug contacting with ear skin.

\* \* \* \* \*